(12) United States Patent
Arar

(10) Patent No.: US 7,615,629 B2
(45) Date of Patent: Nov. 10, 2009

(54) METHODS AND COMPOSITIONS FOR THE TANDEM SYNTHESIS OF TWO OR MORE OLIGONUCLEOTIDES ON THE SAME SOLID SUPPORT

(75) Inventor: Khalil Arar, Meudon (FR)

(73) Assignee: Sigma-Aldrich Co., St. Louis, MO (US)

( * ) Notice: Subject to any disclaimer, the term of this patent is extended or adjusted under 35 U.S.C. 154(b) by 601 days.

(21) Appl. No.: 10/250,492

(22) PCT Filed: Dec. 31, 2002

(86) PCT No.: PCT/EP02/14905

§ 371 (c)(1),
(2), (4) Date: Jul. 29, 2003

(87) PCT Pub. No.: WO2004/058794

PCT Pub. Date: Jul. 15, 2004

(65) Prior Publication Data

US 2006/0149046 A1    Jul. 6, 2006

(51) Int. Cl.
C07H 13/02 (2006.01)
C07H 15/04 (2006.01)
C07H 19/16 (2006.01)

(52) U.S. Cl. ............ 536/116; 536/27.21; 536/119

(58) Field of Classification Search .......... None
See application file for complete search history.

(56) References Cited

U.S. PATENT DOCUMENTS

| | | | |
|---|---|---|---|
| 4,291,024 A | 9/1981 | Turcotte | |
| 4,349,552 A | 9/1982 | Takaya et al. | |
| 4,415,732 A | 11/1983 | Caruthers et al. | |
| 4,458,066 A | 7/1984 | Caruthers et al. | |
| 4,616,071 A | 10/1986 | Holubka | |
| 4,725,677 A | 2/1988 | Koster et al. | |
| 5,049,656 A | 9/1991 | Lewis et al. | |
| 5,093,232 A | 3/1992 | Urdea et al. | |
| 5,118,800 A | 6/1992 | Smith et al. | |
| 5,118,802 A | 6/1992 | Smith et al. | |
| 5,200,514 A | 4/1993 | Chu | |
| 5,221,736 A | 6/1993 | Coolidge et al. | |
| 5,393,877 A | 2/1995 | McLean et al. | |
| 5,420,276 A | 5/1995 | Norbeck | |
| 5,464,759 A | 11/1995 | Coolidge et al. | |
| 5,466,786 A | 11/1995 | Buhr et al. | |
| 5,539,082 A | 7/1996 | Nielsen et al. | |
| 5,552,535 A | 9/1996 | McLean et al. | |
| 5,576,429 A | 11/1996 | Johansson et al. | |
| 5,580,697 A | 12/1996 | Keana et al. | |
| 5,869,696 A * | 2/1999 | Reddy et al. ............. | 548/564 |
| 5,874,532 A | 2/1999 | Pieken et al. | |
| 6,090,932 A | 7/2000 | McGee et al. | |
| 6,107,479 A | 8/2000 | Natt et al. | |
| 6,140,493 A * | 10/2000 | Dower et al. ............ | 506/32 |
| 6,171,797 B1 | 1/2001 | Perbost | |
| 6,262,251 B1 | 7/2001 | Pieken et al. | |
| 6,368,874 B1 | 4/2002 | Gallop et al. | |

FOREIGN PATENT DOCUMENTS

| | | |
|---|---|---|
| DE | 25 31 257 | 1/1976 |
| DE | 29 31 233 | 2/1981 |
| EP | 0 453 247 A2 | 10/1991 |
| EP | 0 294 196 B1 | 3/1996 |
| EP | 0 982 311 A2 | 3/2000 |
| WO | WO 91/06556 | 5/1991 |
| WO | WO 91/10671 | 7/1991 |
| WO | WO 91/13900 | 9/1991 |
| WO | WO 92/06103 | 4/1992 |

(Continued)

OTHER PUBLICATIONS

Farcy, et al. "A Pentaerythritol-Based Molecular Scaffold for Solid-Phase Combinatorial Chemistry," Organic Letters 2001, vol. 3, No. 26, 4299-4301.*
Blackwell, et al. "Exploiting Site-Site Interactions on Solid Support to Generate Dimeric Molecules," Organic Letters 2001, vol. 3, No. 8, pp. 1185-1188.*
U.S. Appl. No. 09/845,742, filed May 1, 2001, Pieken et al.
Agrawal and Khorana (May 1972) J. of the American Chem. Society 94(10):3578-3585.
Andrus et al. (1988) Tetrahedron Letters 29:861-864.
Bannwarth and Wippler (1990) Helv. Chim. Acta 73:1139-1147.
Bayer and Mutter (Jun. 1972) Nature 237;512-513.

(Continued)

Primary Examiner—Shaojia Anna Jiang
Assistant Examiner—Layla Bland

(57) ABSTRACT

The present invention relates to novel methods and novel solid support materials for the tandem synthesis of two or more different oligonucleotides on the same solid support in one synthetic run. The methods involve novel support preparations comprised of two or more types of orthogonally protected anchor groups. Subsequent to the selective removal of the first of the respective protective groups, the first oligonucleotide is assembled on the deblocked anchor groups according to standard methods, preferably via phosphoramidite chemistry. Following the capping of said first oligonucleotide, the anchor groups blocked by a second type of protective group are selectively liberated and serve as the starting point for the assembly of a second oligonucleotide, and so forth. After completion of all the syntheses on the solid support, the oligonucleotides are released from the solid support and deprotected at the nucleobases, using standard methods. Preparations obtained using the method of this invention, generally contain two or more different oligonucleotides. Such preparations are particularly useful in applications that require pairs of oligonucleotide primers, several probes at a time, duplexed nucleic acid fragments, or other combinations of oligonucleotides that are useful in applications such as PCR, sequencing, multiplexed genotyping, cloning and RNA interference. The invention includes procedures for the preparation of the novel solid supports of the invention.

10 Claims, 10 Drawing Sheets

FOREIGN PATENT DOCUMENTS

| | | |
|---|---|---|
| WO | WO 94/13789 | 6/1994 |
| WO | WO 95/24185 | 9/1995 |
| WO | WO 96/34984 | 11/1996 |
| WO | WO 97/14706 | 4/1997 |
| WO | WO 9741139 A2 * | 11/1997 |
| WO | WO 98/30575 | 7/1998 |
| WO | WO 98/30578 A | 7/1998 |
| WO | WO 98/47910 A | 10/1998 |
| WO | WO 01/84234 | 11/2001 |
| WO | WO 01/96357 A2 | 12/2001 |
| WO | WO/02-16022 A2 | 2/2002 |
| WO | WO 02/20541 A2 | 3/2002 |

OTHER PUBLICATIONS

Beaucage and Iyer (1993) Tetrahedron 49(10):1925-1963.
Blackburn and Guo (1992) Tetrahedron Letters 34(1):149-152.
Duggan and Imagire (Feb. 1989) Synthesis 131-132.
Eadie and Davidson (1987) Nucleic Acid Research 15(20):8333-8349.
Hill et al. (2001) J. Org. Chem. 66:5352-5358.
March, J. ed. (1992) in *Advanced Organic Chemistry* 839-852.
Natt and Häner (1997) Tetrahedron 53(28):9629-9636.
Rideout and Breslow. (1980) J. Am. Chem. Soc. 102:7816-7817.
Yu et al. (1994) Tetrahedron Letters 35:8565-8568.
Beaucage and Iyer (1992) Tetrahedron 48:2223-2311.
Fischer et al. (1990) BioTechniques 9:300-301.
Gryaznov et al. (1995) Proc. Nat. Acad. Sci. 92:5798-5802.
Hardy et al. (1994) Nucleic Acids Res. 22:2998-3004.
Johnson et al. (1990) BioTechniques 8:424-428.
Kumar and Poonian (1984) J. Org. Chem. 49:4905-12.
McBride and Caruthers (1983) Tetrahedron Letters 24:245-248.
McBride et al. (1988) BioTechniques 6:362-367.
Micklefield (2001) Current Medicinal Chemistry 8:1157-1179.
Ono et al. (1995) Nucleic Acids Res. 23:4677-82.
Reddy et al. (1987) Tetrahedron Letters 28:23-26.
Robles et al. (1995) Nucleic Acids Res. 23:4151-61.
Sinha et al. (1983) Tetrahedron Letters 24:5843-5846.
Aurup et al. (1992) Biochemistry 31:9636-9641.
Bruick et al. (Jan. 1996) Chemistry & Biology 3:49-56.
Bruick et al. (1997) Nucleic Acids Res. 25:1309-1310.
Englisch and Gauss (Jun. 1991) Angew. Chem. Int. Ed. Engl. 30:613-627.
Eritja et al. (1991) Tetrahedron 47: 4113-4120.
Goodchild (May/Jun. 1990) Bioconjugate Chemisty 1:166-187.
Giuliano et al. (1993) *J. Org. Chem.* 58:4979-4988.
Giuliano et al. (1990) *J. Org. Chem.* 55:3555-3562.
Haralambidis et al. (1990) Nucleic Acids Res. 18:493-499.
Haralambidis et al. (1987) Tetrahedron Lett. 28:5199-5202.
Huryn and Okabe (1992) Chemical Reviews 92:1745-1768.
Jager et al. (1995) *Tetrahedron Letters* 36:861-864.
Jones et al. (1995) J. Med. Chem. 38:2138-2144.
Juby et al. (1991) Tetrahedron Lett. 32:879-822-882.
Koch et al. (2000) Bioconjugate Chem. 11:474-483.
Koch et al. (1999) Polystyrene or polycarbonate plates/anthraquinone oligos or cDNA with irradiation, Exiqon.
Krieg et al. (1991) Antisense Res. and Dev. 1:161-171.
Leonetti et al. (1990) Bioconjugate Chem. 1:149-153.
Lubineau et al. (1995) *Carbohydrate Research* 270:163-170.
Ludwig and Eckstein (1989) J. Org. Chem. 54:631-635.
Mikhailopulo et al. (1993) Liebigs Ann. Chem. pp. 513-519.
Mori et al. (1989) Nucleosides & Nucleotides 8:649-657.
Nishikubo et al. (1981) Tetrahedron Letters 22:3873-3874.
Roush et al. (1983) Tetrahedron Letters 24:1377-1380.
Schmidt (1994) Synlett 4:241-242.
Shibuya and Ueda (1980) Chem. Pharm. Bull. 28:939-946.
Sinha and Cook (1988) Nucleic Acids Res. 16:2659-2669.
Smith et al. (1987) Methods in Enzymology, 155:260-301.
Sproat et al. (1987) Nucleic Acids Research 15:6181-6188.
Theisen et al. (1992) Tetrahedron Lett. 33:5033-5036.
Tronchet et al. (1990) Tetrahedron Letters 31:531-534.
Tronchet et al. (1988) Nucleosides & Nucleotides 7:249-269.
Tung (1991) Bioconjugate Chem. 2:464-465.
Verheyden et al. (1971) J. Org. Chem. 36:250-254.
Wagner et al. (1991) Nucleic Acids Res. 19:5965-5971.
Warshaw et al. (1990) J. Med. Chem. 33:1663-1666.
Zalipsky (1995) Bioconjugate Chem. 6:150-165.

* cited by examiner

SEQUENCE LISTING

```
<160> NUMBER OF SEQ ID NOS: 19

<210> SEQ ID NO 1
<211> LENGTH: 10
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(10)

<400> SEQUENCE: 1
gggtgttgtc                                                         10

<210> SEQ ID NO 2
<211> LENGTH: 13
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(13)

<400> SEQUENCE: 2
gcttacattt tag                                                     13

<210> SEQ ID NO 3
<211> LENGTH: 12
```

```
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(12)

<400> SEQUENCE: 3
tctttacact tc                                                          12

<210> SEQ ID NO 4
<211> LENGTH: 15
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(15)

<400> SEQUENCE: 4
tctaacaggg tgttg                                                       15

<210> SEQ ID NO 5
<211> LENGTH: 12
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(12)

<400> SEQUENCE: 5
ttctagttat cg                                                          12

<210> SEQ ID NO 6
<211> LENGTH: 23
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(23)

<400> SEQUENCE: 6
catctgtagt ctttcacctg ttt                                              23

<210> SEQ ID NO 7
<211> LENGTH: 25
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(25)

<400> SEQUENCE: 7
acctcacaag atgttcaaaa gccat                                            25

<210> SEQ ID NO 8
<211> LENGTH: 25
<212> TYPE: DNA
<213> ORGANISM: Artificial
<220> FEATURE:
<223> OTHER INFORMATION: Synthetic Nucleic Acid Ligand
```

```
<220> FEATURE:
<221> NAME/KEY: misc_feature
<222> LOCATION: (1)..(25)

<400> SEQUENCE: 8
taatctgtgt gcttacattt taggg                                        25

<210> SEQ ID NO 9
<211> LENGTH: 23
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(23)

<400> SEQUENCE: 9
ttcattgcta ctggggtgtt gtc                                          23

<210> SEQ ID NO 10
<211> LENGTH: 24
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(24)

<400> SEQUENCE: 10
gctttcatca agtttatccc aacc                                         24

<210> SEQ ID NO 11
<211> LENGTH: 26
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(26)

<400> SEQUENCE: 11
cccatcaatc tttttcttta cacttc                                       26

<210> SEQ ID NO 12
<211> LENGTH: 12
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(12)

<400> SEQUENCE: 12
tttttttttt tt                                                      12

<210> SEQ ID NO 13
<211> LENGTH: 15
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(15)
```

-continued

```
<400> SEQUENCE: 13 ttttttttttt ttttt                                                          15

<210> SEQ ID NO 14
<211> LENGTH: 31
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(31)

<400> SEQUENCE: 14
acgttggatg gtcttcagag acatagttaa g                                         31

<210> SEQ ID NO 15
<211> LENGTH: 31
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(31)

<400> SEQUENCE: 15
acgttggatg gtggagtaag agtaaatgtc c                                         31

<210> SEQ ID NO 16
<211> LENGTH: 25
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(25)

<400> SEQUENCE: 16
gcgaccgagc ctgacctcca gtccg                                                25

<210> SEQ ID NO 17
<211> LENGTH: 25
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(25)

<400> SEQUENCE: 17
cggactggag gtcaggctcg gtcgc                                                25

<210> SEQ ID NO 18
<211> LENGTH: 25
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(25)

<400> SEQUENCE: 18
acgctgccag tcacggcgac cgctc                                                25
```

```
<210> SEQ ID NO 19
<211> LENGTH: 25
<212> TYPE: DNA
<213> ORGANISM: Artificial
<220> FEATURE:
<223> OTHER INFORMATION: Synthetic Nucleic Acid Ligand
<220> FEATURE:
<221> NAME/KEY: misc_feature
<222> LOCATION: (1)..(25)

<400> SEQUENCE: 19
gagcggtcgc cgtgactggc agcgt                                          25
```

METHODS AND COMPOSITIONS FOR THE TANDEM SYNTHESIS OF TWO OR MORE OLIGONUCLEOTIDES ON THE SAME SOLID SUPPORT

FIELD OF INVENTION

The present invention is related to the field of nucleotide chemistry. More specifically, the present invention is related to oligonucleotide synthesis. Even more specifically, the present invention is related to the serial synthesis of two or more different oligonucleotides on the same solid support in one synthetic run.

BACKGROUND OF THE INVENTION

The enormous increase in the demand for synthetic oligonucleotides, fueled by the advances in DNA technology, has been even further increased by recent progress in sequencing and decoding whole genomes, in particular the human genome. Many of the methods employed in molecular biology and DNA-based diagnostics to amplify, detect, analyze and quantify nucleic acids are dependent on chemically synthesized oligonucleotides. For instance, chemically synthesized oligonucleotides are employed in recombinant host-vector systems, which are used for techniques such as site-directed mutagenesis. They are also used in PCR methods, in which oligonucleotide primers are employed in temperature-cycled enzymatic amplifications of nucleic acids. Primers are also needed for state of the art sequencing techniques featuring enzymatic elongation and random termination. Another rapidly growing field is the application of oligonucleotides in hybridization assays, which are based on the specific annealing of oligonucleotide probes to the region of a nucleic acid analyte having a complementary sequence. Probes with covalently conjugated dyes that generate a fluorescent signal upon a perfect match hybridization are among the latest developments in this field. Corresponding methods to test for specific genomic epitopes, such as allelic discrimination or SNP detection employ hybridization probes and are readily multiplexable. Thus, automated high-throughput setups capable of simultaneously screening a vast number of analytes using miniaturized arrays of hybridization probes, such as DNA chips, are used for applications like genotyping and expression profiling. These and related methods will likely have an enormous impact in the areas of drug development and health management, among others.

Antisense technology is another field that demands a rapidly increasing supply of oligonucleotides. Synthetic antisense oligonucleotides are complementary to an RNA or DNA target sequence and are designed to halt a biological event, such as transcription, translation or splicing. They represent a whole new class of therapeutic agents, which have been shown to exhibit antiviral activity by inhibiting viral DNA or protein synthesis and, moreover, may be able to cure certain diseases by inhibiting gene expression via specifically recognizing and binding mRNA. The most recent generation of antisense oligonucleotides are comprised of backbone-modified DNA or RNA derivatives such as 2'-OMe-RNA, phoshorothioate, morpholino nucleic acid, LNA, or combinations thereof. In this manner, the properties of antisense compounds, such as nuclease resistance, RNase H susceptibility and binding affinity, which are crucial for either blocking or promoting the degradation of the complementary mRNA, can be modulated and optimized.

Another process of posttranscriptional, sequence-specific gene silencing is RNA interference (RNAi), which is presently being intensely investigated. RNAi is initiated inside cells by small interfering RNAs (siRNA), which are double-stranded RNA oligomers having 20 to 23 base pairs. The RNAi process has been utilized for functional analysis of mammalian genes and might also allow therapeutic applications.

The present state of the art for conducting automated oligonucleotide synthesis is the solid phase approach using phosphoramidite chemistry, which is based on the developments of Caruthers et al. (see e.g., McBride and Caruthers (1983) Tetrahedron Letters 24:245-248; Caruthers et al. U.S. Pat. Nos. 4,415,732 and 4,458,066) and Sinha et al. ((1983) Tetrahedron Letters 24:5843-5846) and which has been, together with related methods, such as the hydrogen-phosphonate chemistry, extensively reviewed by Beaucage and Iyer (1992) Tetrahedron 48:2223-2311. Each of these references is specifically incorporated herein by reference in its entirety.

During phosphoramidite mediated chemical oligonucleotide synthesis a series of nucleotide synthons are sequentially attached in a predetermined order to either, depending on the direction of chain extension, the 5'-functional group or the 3'-functional group of the growing strand, which is linked to a solid phase, such as CPG or a polystyrene resin. The attachment of each synthon generally comprises the following steps: 1) deprotecting the functional group of the growing strand, commonly the 5'-hydroxyl group; 2) coupling by adding a nucleoside synthon and an activator; 3) capping of unreacted terminal functional groups through introduction of an inert protecting group, to prevent further coupling to failure sequences; and 4) oxidizing the newly formed internucleosidic phosphorous linkage to the naturally occurring pentavalent state. This synthetic scheme, applying phosphoramidite chemistry, has reached a high level of optimization featuring routine stepwise coupling efficiencies of up to 99% on average per cycle. Following the completed assembly of the desired sequence the oligonucleotide is finally released and deprotected at the nucleobases usually in one step employing basic conditions.

In order to cope with the rapidly increasing demand for oligonucleotides, improvements in the currently available synthetic procedures are highly desirable, particularly to increase the number of oligonucleotides produced per day and per synthesizer. Promising approaches to enhance the throughput rate of oligonucleotides produced are methods that allow for the synthesis of not one, but two or more oligonucleotides in one synthetic run on a single batch of solid support. In this way, time and expense per oligonucleotide are greatly reduced due to lower amounts of support needed and lower numbers of samples that have to be handled, processed and stored. This strategy is especially favorable in cases in which all of the oligonucleotides produced in one synthetic run can be or even need to be added to the final application at the same time. This applies particularly to primer pairs as used for PCR or sequencing and for double stranded DNA or RNA probes. These combined oligonucleotide preparations also lead to a reduced number of samples to be stored and handled for the final application.

To date, prior art methods applying the strategy of the combined synthesis of oligonucleotides on the same support are all based upon the serial assembly at the same anchor moiety. The oligonucleotides are therefore, interconnected by cleavable linkers and thus are all simultaneously released in the final cleavage/deprotection step. For example, Hardy et al. (1994) Nucleic Acids Res. 22:2998-3004 and McLean et al. U.S. Pat. Nos. 5,393,877 and 5,552,535, each of which is specifically incorporated herein by reference in its entirety, have introduced the "TOPS" (two oligonucleotides per synthesis) methodology, which is based on a linker featuring a phosphoramidite moiety and a DMT group. In the course of the automated assembly using, possibly modified, standard procedures for coupling phosphoramidite monomers the linker can be integrated into the oligomeric chain partitioning it into the desired oligonucleotide units. One major drawback of the TOPS method is the harsh conditions and the long reaction times required to cleave the products from the linker (concentrated ammonia, 80° C., overnight; alternatively: conc. ammonia/40% aqueous methylamine (1:1, v/v), 60° C., 8 hours).

A modification of this technique is described by Pon et al. (WO 02/20541) and Holland et al., (WO 92/06103). Each of these references is specifically incorporated herein by reference in its entirety. Instead of the aforementioned separate linker amidite monomers, which are attached in a separate coupling cycle, in this method a linker unit is introduced as part of the modified nucleoside phosphoramidites. One of the oligonucleotides produced by this method necessarily carries a 5'-terminal phosphate group and is therefore not useful for some biochemical applications.

Each of the above-described methods for the tandem synthesis of oligonucleotides, include the coupling of specialty amidites, which is usually not very efficient and requires elongated coupling times or even repeated coupling. Another drawback of both methods is the need to prepare the specialty amidites. The synthesis of such linkers or modified nucleoside amidites is generally lengthy and time consuming. In addition, spare synthesizer ports are required on an automated nucleic acid synthesizer to introduce the specialty amidites into the synthetic process. Also, both methods result in an increasing number of truncated sequences and decreasing coupling efficiencies as the oligomer chain length progresses. Thus, the oligonucleotide units positioned closer to the end of the chain are of deteriorating quality and diminishing concentration. Thus, there remains a need for an improved method for the tandem synthesis of oligonucleotides.

SUMMARY OF THE INVENTION

The present invention includes a novel method for the combined, serial synthesis of two or more different oligonucleotides on the same solid support in one synthetic run, referred to hereinafter as "tandem synthesis." Briefly, the method of the present invention comprises the steps of: a) providing a solid support, wherein said solid support is comprised of anchor groups that are protected by two or more orthogonal protective groups; b) removing one of said orthogonal protective group from the anchor groups; c) synthesizing an oligonucleotide on the deprotected anchor group; d) capping the synthesized oligonucleotide; e) repeating steps b) to d) until all of the orthogonal protective groups are deprotected, wherein step d) is omitted for the last orthogonal protective group; and f) cleaving all synthesized oligonucleotides from the solid support and subjecting them to conditions that are suitable to deprotect the oligonucleotides. Excellent coupling rates and yields are obtained using the method of this invention.

The method of the present invention is based on orthogonally protected anchor groups situated on the solid support of the invention, each of which is successively used to synthesize one of the desired sequences, as outlined in FIGS. 1 and 2. Subsequent to the selective removal of the first of the respective protective groups, the first oligonucleotide is assembled on the deblocked anchor groups according to standard methods for the solid phase synthesis of oligonucleotides. In a preferred embodiment, phosphoramidite chemistry is employed to synthesize the oligonucleotide. Following the capping of said first oligonucleotide, the anchor groups blocked by a second type of protective group are selectively liberated, which then serve as the starting point for the assembly of the second oligonucleotide, and so forth. After completion of all of the syntheses on the solid support, the synthesized oligonucleotides are further processed as a mixture during the release and deprotection steps. Preparations obtained using the method of this invention, contain a mixture of two or more oligonucleotides. They are particularly useful in applications that require pairs of oligonucleotide primers, several probes at a time, duplexed nucleic acid fragments and the like, including but not limited to PCR, sequencing, multiplexed genotyping, cloning and RNA interference.

In one embodiment of the invention, one of the anchor groups may be unprotected. In this embodiment the method of the invention comprises the steps of: a) providing a solid support, wherein said solid support is comprised of anchor groups that are partially unprotected, the remainder of the anchor groups being protected by one or more protective groups, the protective groups being orthogonal to each other in case more than one protective group is employed; b) synthesizing an oligonucleotide on the unprotected anchor groups; c) capping the synthesized oligonucleotide; d) removing one protective group from the anchor groups; e) synthesizing an oligonucleotide on the deprotected anchor groups; f) repeating steps c) to e) until all of the orthogonal protective groups are deprotected; and g) cleaving all synthesized oligonucleotides from the support.

The methods disclosed herein are applicable to solid phase oligonucleotide synthetic schemes in which the growing oligonucleotide chain is built in the 3' to 5' direction, as well as, in solid phase oligonucleotide synthetic schemes in which the growing oligonucleotide chain is built in the 5' to 3' direction. The methods disclosed herein can be applied either with or without removing the final terminal protective group following the synthesis of the last assembled oligonucleotide. In the former case, all of the oligonucleotides synthesized are jointly processed through all work-up steps and transferred in combination to the final application. In the latter case, by utilizing the terminal protective group as a handle the last oligonucleotide synthesized may be separated, i.e. by employing the commonly used terminal dimethoxytrityl group as a handle in a simple, reversed-phase cartridge based purification step.

The methods of this invention can be applied to any known methods for the solid phase synthesis of oligonucleotides including, but not limited to phosphoramidite chemistry, H-phosphonate chemistry, phosphotriester chemistry, or any other synthetic chemistry utilized to prepare oligonucleotides on solid supports. Furthermore the methods of the invention can be adapted to universal linker systems, as well as, to those preloaded with the first nucleoside of the oligonucleotide to be synthesized.

Included in the present invention are novel solid support preparations useful for applying the method of this invention, as well as, procedures for their preparation. The methods of this invention employ solid support preparations comprised of two or more types of orthogonally protected anchor groups, which enables the tandem synthesis of oligonucleotides on the same support without the need for reinitializing the set-up between each synthetic run, in particular exchanging the solid support container and re-programming the synthesizer. In addition, oligonucleotides synthesized on the same support by methods of the invention in most instances can be subjected to joint work-up steps including cleavage, purification, desalting and concentration. Finally, they can be directly employed to most of the relevant ultimate applications, as their 3'- and 5'-hydroxyl groups are unmodified, particularly as they do not carry phosphate groups.

In one embodiment of the invention, the solid support is comprised of a homogeneous distribution of orthogonally protected anchor groups, wherein the desired number of oligonucleotides determines the number of different orthogonal anchor groups that are required. In another embodiment of the invention, the solid support is comprised of a mixture of two or more solid support components. In this embodiment, each component carries only one of the orthogonal protective groups and a plurality of orthogonally protected anchor groups is established by mixing two or more components, depending on the desired number of oligonucleotides to be synthesized.

The novel methods and support preparations of this invention have significant advantages and do not suffer from the limitations inherent in the prior art methods. The solid supports described herein provide for a simple, smooth and efficient synthesis of two or more oligonucleotides of consistent quality that are useful for a broad range of applications. The methods of this invention are especially targeted to the cost effective production of oligonucleotides for applications employing two or more primers, probes, duplex nucleic acid fragments or the like. The methods of this invention can easily be adopted in syntheses of modified oligonucleotides, such as phosphorothioates, RNA derivatives and locked nucleic acids (LNA), and oligonucleotides conjugated to e.g. one or several dyes via a linker unit. Due to the simple and generally applicable synthetic process described in the invention, the methods and support preparations are highly suitable for an automated setup.

The methods of the present invention enable an increase in the rate at which oligonucleotide can be prepared and a reduction in the costs involved, due to less expenditures required for handling and processing, as well as, for consumables and solid supports. The methods of the invention do not lead to compromised product quality, since the process of oligonucleotide assembly as such is based solely on the highly optimized, established procedures of the art and do not require modifications, such as specialty amidites.

BRIEF DESCRIPTIONS OF THE DRAWINGS

Figure 5:
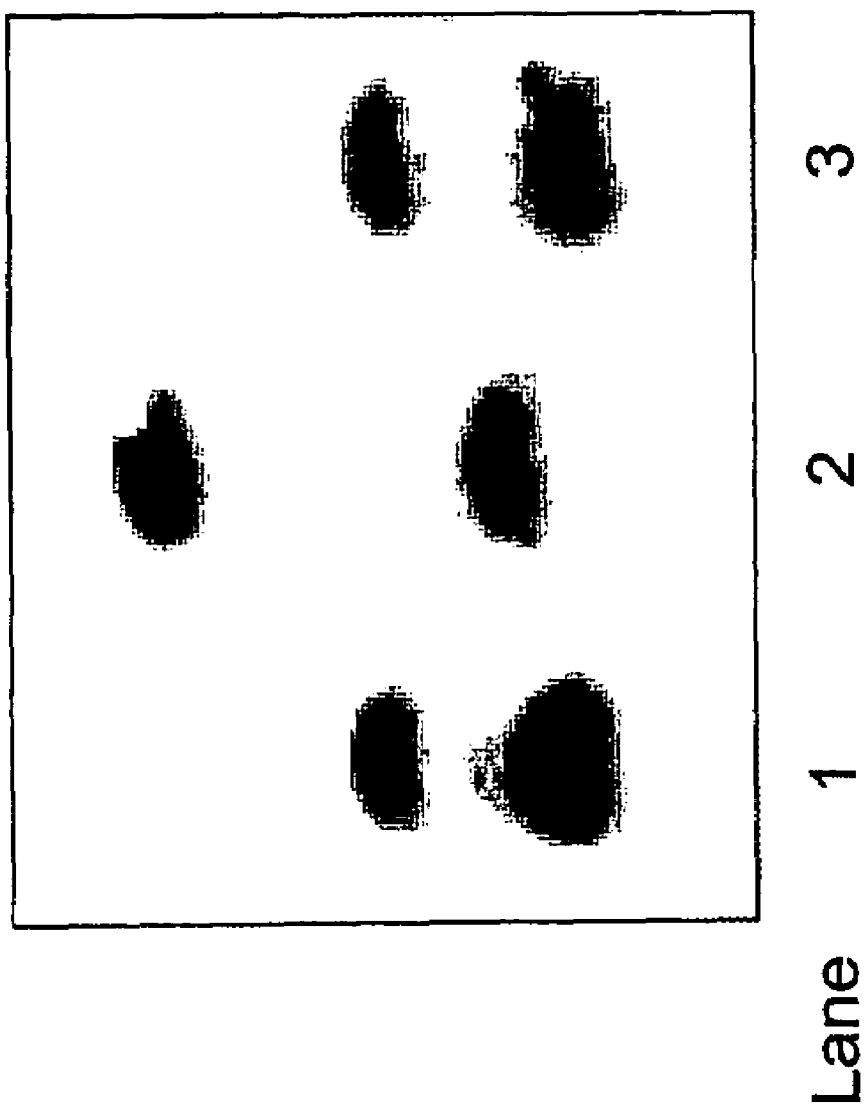

FIG. 5 displays the electrophoretic analysis of the tandem synthesis of primer pairs 1 to 3, synthesized as described in Example 6. Lanes 1, 2 and 3 represent primer pairs 1, 2 and 3, respectively.

Figure 6:
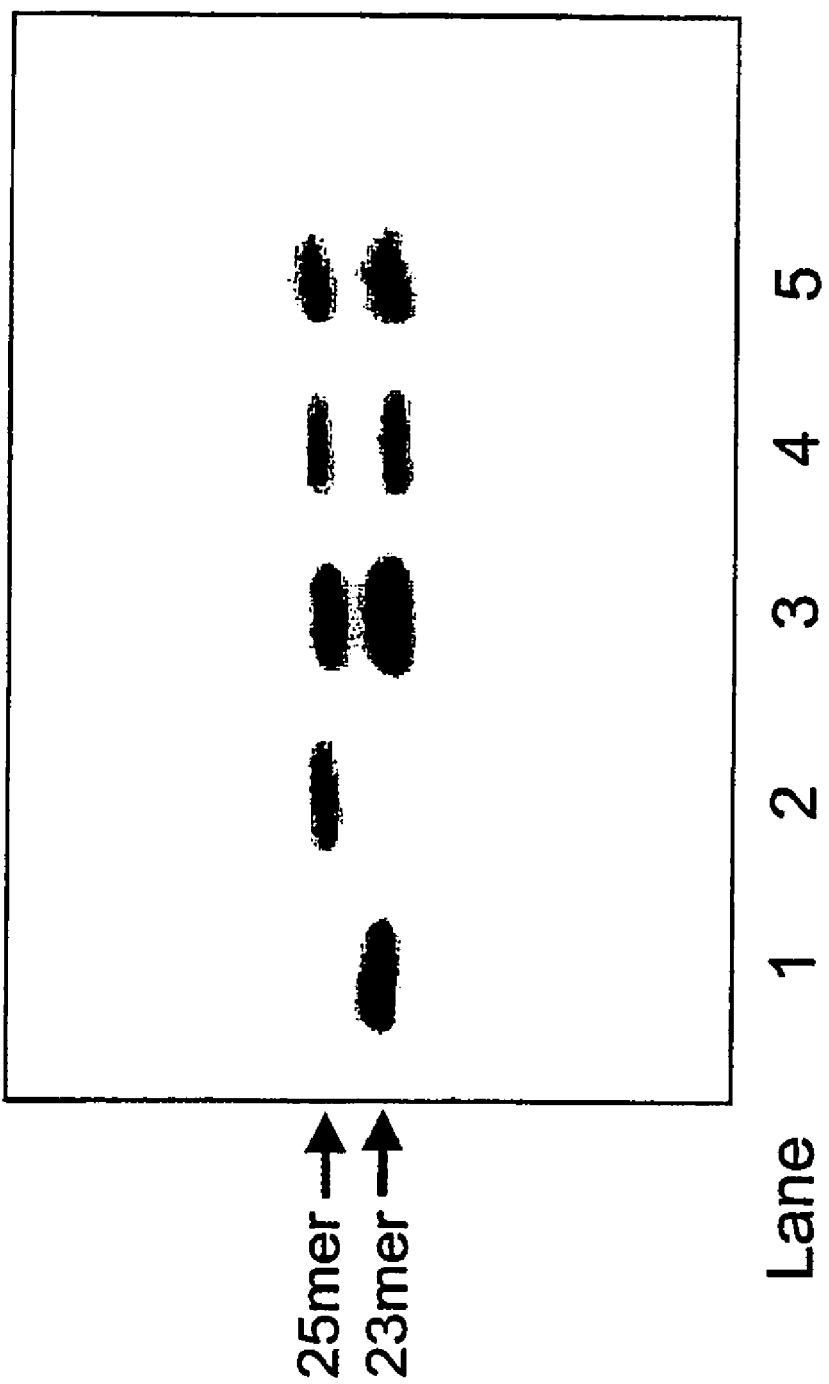

FIG. 6 displays the electrophoretic analysis of the tandem synthesis of a 25mer and a 23mer oligonucleotide as described in Example 7. Lanes 4 and 5 depict the separation of the two tandemly synthesized oligonucleotides. Lanes 1 and 2 represent the 23mer and 25mer, respectively, which were individually synthesized by conventional means, and lane 3 represents the separation of a mixture thereof.

Figure 7:
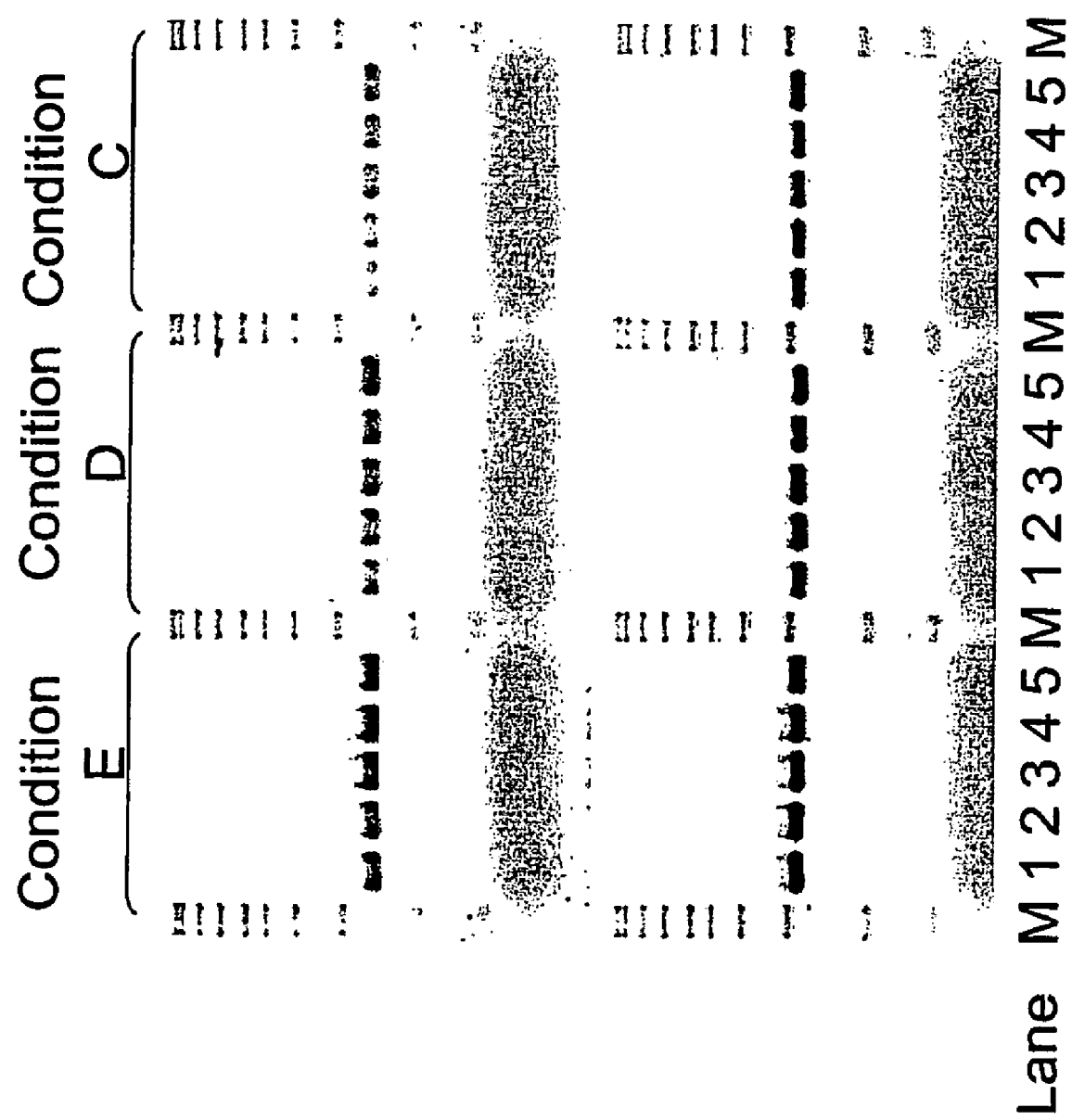

FIG. 7 displays the electrophoretic analysis of the PCR products prepared as described in Example 8. The upper set of gels depicts the results for primer pair #1 applying three different PCR conditions C, D and E: lanes 1 to 4 represent to the primer pair obtained via a tandem oligonucleotide synthesis, lanes 5 represent the primer pair as obtained through conventional SPOS protocols in separate synthesis for each primer and lanes M contain size markers (50 bp ladder). The lower set of gels depicts the results for the primer pair #2 accordingly.

Figure 8:
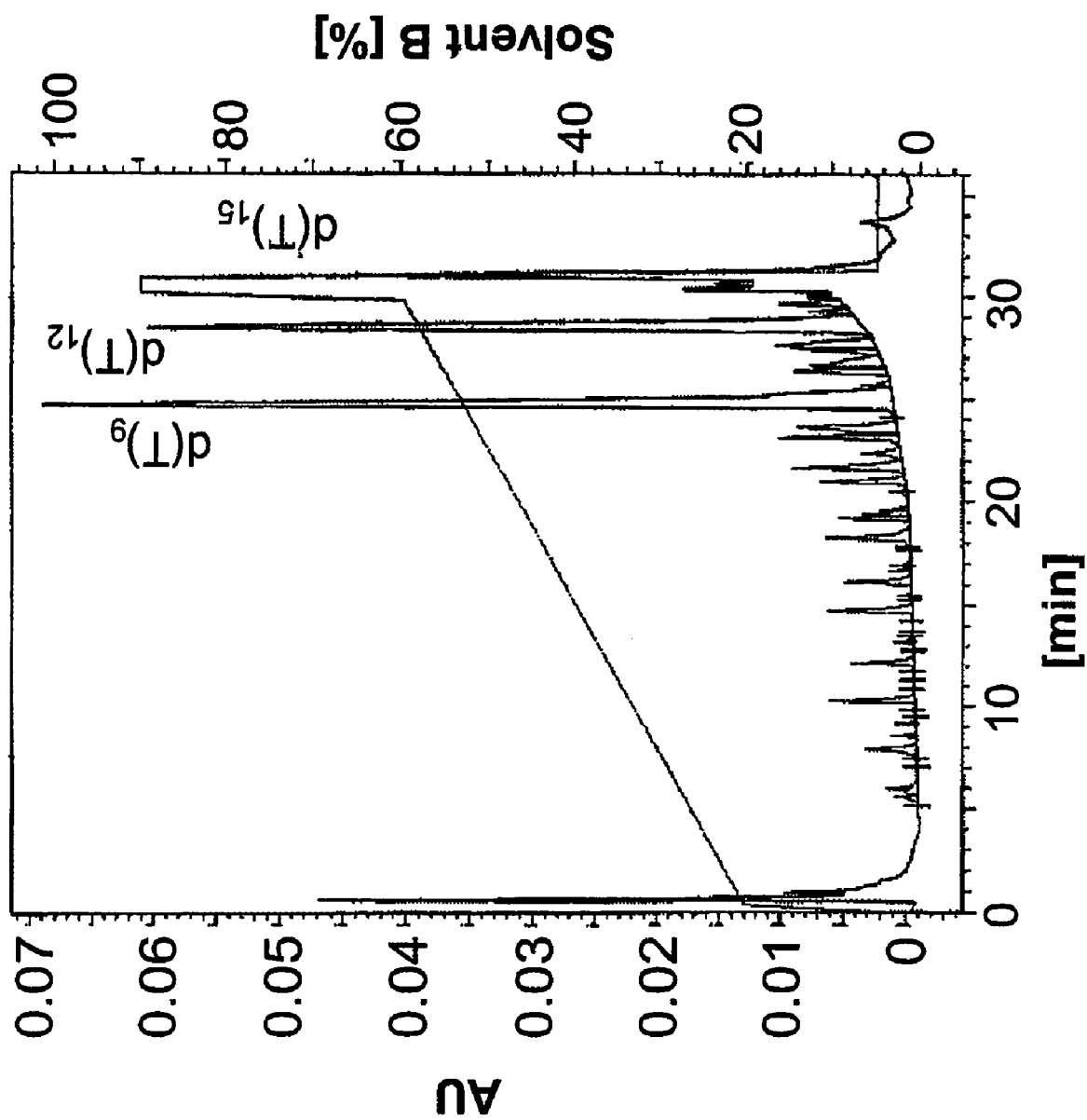

FIG. 8 depicts the AX-HPLC chromatogram of the tandem synthesis of the three oligonucleotides $d(T)_9$, $d(T)_{12}$ and $d(T)_{15}$, as described in Example 9.

FIGS. 9A and B illustrate the RP-HPLC chromatograms according to Example 11. The chromatograms of FIGS. 9A and 9B represent the analyses before and after the purification via preparative gel electrophoresis, respectively.

Figure 10:
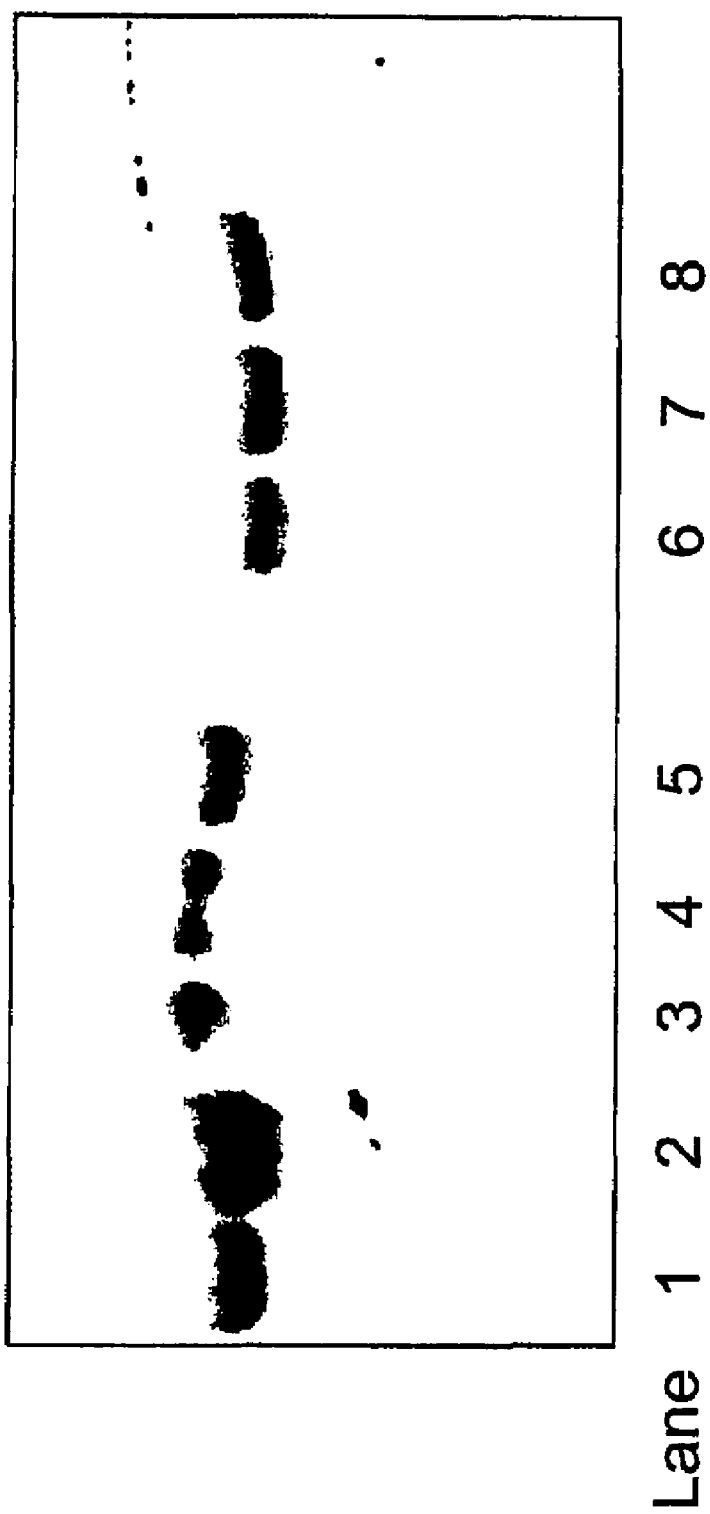

FIG. 10 depicts the electrophoretic analysis under non-denaturing conditions of the tandemly synthesized oligonucleotide duplexes, as described in Example 12. Lanes 1 and 2 represent a 40mer oligonucleotide marker. Lanes 3 to 5 and 6 to 8 relate to the duplexes formed by oligonucleotide pairs 1 and 2, respectively.

DETAILED DESCRIPTION OF THE INVENTION

The present invention includes a novel method for the combined, serial synthesis of two or more different oligonucleotides on the same solid support in one synthetic run, referred to hereinafter as "tandem synthesis." The method of the present invention is based on orthogonally protected anchor groups situated on the solid support of the invention, each of which is successively used to synthesize one of the desired sequences, as outlined in FIGS. 1 and 2. Subsequent to the selective removal of the first of the respective protective groups, the first oligonucleotide is assembled on the deblocked anchor groups according to standard methods for the solid phase synthesis of oligonucleotides. In a preferred embodiment, phosphoramidite chemistry is employed to synthesize the oligonucleotide. Following the capping of said first oligonucleotide, the anchor groups blocked by a second type of protective group are selectively liberated, which then serve as the starting point for the assembly of the second oligonucleotide, and so forth. After completion of all of the desired syntheses on the solid support, the synthesized oligonucleotides are further processed as a mixture during the release and deprotection steps. Preparations obtained using the method of this invention, generally contain a mixture of two or more oligonucleotides.

The methods disclosed herein are applicable to solid phase oligonucleotide synthetic schemes in which the growing oligonucleotide chain is built in the 3' to 5' direction, as well as, in synthetic schemes in which the growing oligonucleotide chain is built in the 5' to 3' direction. The methods of this invention can be applied to any known methods for the solid phase synthesis of oligonucleotides. Furthermore the methods of the invention can be adapted to universal linker systems, as well as, to those preloaded with the first nucleoside of the oligonucleotide to be synthesized.

Included in the present invention are novel solid support preparations useful for applying the method of this invention, as well as, procedures for their preparation. In one embodiment of the invention, the solid support is comprised of a homogeneous distribution of orthogonally protected anchor groups, wherein the desired number of oligonucleotides determines the number of different orthogonal anchor groups that are required. In another embodiment of the invention, the solid support is comprised of a mixture of two or more solid support components. In this embodiment, each component carries only one of the orthogonal protective groups and a plurality of orthogonally protected anchor groups is established by mixing two or more components, depending on the desired number of oligonucleotides to be synthesized.

The novel methods and support preparations of this invention have significant advantages and do not suffer from the limitations inherent in the prior art methods. The solid supports described herein provide for the simple, smooth and efficient synthesis of two or more oligonucleotides of consistent quality that are useful for a broad range of applications. The methods of this invention can easily be extended to the synthesis of modified oligonucleotides, such as phosphorothioates, RNA derivatives and locked nucleic acids (LNA), and oligonucleotides conjugated to e.g. one or several dyes via a linker unit. Due to the simple and generally applicable synthetic process described in the invention, the methods and support preparations are highly suitable for an automated setup.

Various terms are used herein to refer to aspects of the present invention. To aid in the clarification of the description of the components of the invention, the following descriptions are provided.

It is to be noted that the term "a" or "an" entity refers to one or more of that entity; for example, an oligonucleotide refers to one or more oligonucleotides. As such, the terms "a" or "an," "one or more" and "at least one," are used interchangeably herein.

The term "oligonucleotide synthesis" as used herein refers to solid phase oligonucleotide synthesis (SPOS) using any methods known to those of skill in the art. Preferably, the SPOS is performed using methodology including, but not limited to either phosphoramidite, phosphotriester and/or nucleoside hydrogen phosphonate chemistries known to those skilled in the art as described e.g., by Gait, ed. (1984) in *Oligonucleotide Synthesis: A Practical Approach*, IRL Press, Oxford, UK; Eckstein, ed., (1991) in *Oligonucleotides and Analogs: A Practical Approach*, IRL Press, Oxford, UK; Beaucage and Iyer (1992) Tetrahedron 48:2223-2311; McBride and Caruthers (1983) Tetrahedron Letters 24:245-248 and Sinha et al. (1983) Tetrahedron Letters 24:5843-5846, each of which is specifically incorporated herein by reference in its entirety. The method of this invention, however, can be extended to any other chemistry used in solid phase oligonucleotide synthesis. Typically, oligonucleotide synthesis involves a number of chemical steps that are performed in a cyclical repetitive manner throughout the synthesis, each cycle adding one nucleotide synthon to the growing oligonucleotide chain. The standard chemical steps involved in a cycle include a deprotection step that liberates a functional group for further chain elongation, a coupling step that incorporates a nucleotide synthon into the oligonucleotide to be synthesized, and other steps as required by the particular chemistry used in the oligonucleotide synthesis, e.g. an oxidation step as required with phosphoramidite chemistry etc. Optionally, a capping step that blocks those functional groups that were not elongated in the coupling step is inserted in the cycle.

The extension of the oligonucleotide chain in the course of an oligonucleotide synthesis is typically performed in the 3' to 5' direction by adding nucleotide synthons carrying a suitable protective group at the 5'-position, e.g. the widely employed DMT-group (DMT=dimethoxytrityl=bis(4-methoxyphenyl) phenylmethyl), and a suitable activatable group, e.g. a phosphoramidite group, at the 3'-position to form a linkage to the 5'-position of the growing chain. The extension of the oligonucleotide chain may alternatively be pursued in the 5' to 3' direction by adding nucleotide synthons in the coupling reaction that carry suitable protective groups at the 3'-position, e.g. a DMT-group, and a suitable activatable group, e.g. a phosphoramidite group, at the 5'-position to form a linkage to the 3'-position of the growing chain. This approach is exemplified in the synthesis of oligodesoxynucleotides with 3'-DMT protected deoxynucleoside 5'-phosphoramidites, as described by e.g. Robles et al. (1995) Nucleic Acids Res. 23:4151-61, which is incorporated herein by reference in its entirety, or in the synthesis of N3'-P5' phosphoramidite oligonucleotides with N3'-trityl protected nucleoside 5'-phosphoramidites, as described e.g. by Gryaznov et al. (1995) Proc. Nat. Acad. Sci. 92:5798-5802, which is incorporated herein by reference in its entirety.

Nucleotide synthons used in the coupling step of an oligonucleotide synthesis cycle typically are mononucleotide synthons, e.g. the commercially available 5'-DMT protected deoxynucleoside 3'-phosphoramidites. Nucleotide synthons also include, but are not limited to, dinucleotide synthons, as described by Kumar and Poonian (1984) J. Org. Chem. 49:4905-12, which is incorporated herein by reference in its entirety, trinucleotide synthons, as described by Ono et al. (1995) Nucleic Acids Res. 23:4677-82, which is incorporated herein by reference in its entirety, or synthons that consist of more than 3 nucleotide units.

As used herein the term "oligonucleotide" refers to a single stranded chain of either deoxyribonucleotides or ribonucleotides or chemical modifications thereof, such as e.g. nucleotides with a O2'-C4'-methylene bridge in their sugar portion, which are the constituting nucleotides of locked nucleic acids (LNA). Modifications include, but are not limited to those that provide other chemical groups that incorporate additional charge, polarizability, hydrogen bonding, electrostatic interaction, and functionality to the individual nucleotides or their corresponding bases or to the oligonucleotides as a whole. Such modifications include, but are not limited to modified bases such as 2'-position sugar modifications, e.g. 2'-O-methyl or 2'-fluoro modifications, 5-position pyrimidine modifications, 8-position purine modifications, modifications at cytosine exocyclic amines, incorporation of 5-bromouracil; backbone modifications, methylations, bases that can be part of unusual base-pairing combinations, such as the isobases isocytidine and isoguanidine and the like. Modifications further include attached labels and reporter molecules, such as fluorescent dyes, biotin, minor groove binders and the like that are known to those skilled in the art. In addition, modifications include modified backbones of the oligonucleotides, examples being peptide nucleic acids (PNA), phosphorothioate DNA, methylphosphonate DNA and other modifications known to those skilled in the art and reviewed by Micklefield (2001) Current Medicinal Chemistry 8:1157-1179, which is incorporated herein by reference in its entirety. Oligonucleotides, as referred to in this invention are comprised of any combinations of the nucleotides and their modifications described above and can have either a few, e.g. up to 20, or many, e.g. 20 to several hundred or more, nucleotides incorporated in their chain, the total number of nucleotides being denoted "n" in the context of this invention. In one embodiment, the oligonucleotides of this invention are comprised of from about 20 to about 1000 nucleotides.

The term "solid phase" as used herein refers to a polymer, which is insoluble in the medium employed in a particular reaction or unit operation performed to synthesize or purify oligonucleotides. A solid phase can be an inorganic polymer, including, but not limited to inorganic oxides, such as silica, alumina, zeolites and controlled pore glass (CPG), a modified inorganic polymer, such as silica or CPG modified with an organic coating, e.g. aminopropyl-silane derivatized silica or aminopropyl-silane derivatized CPG, or an organic polymer, including, but not limited to polystyrene, polyacrylamide, polymethacrylate, polyvinylalcohol, or other synthetic polymers, carbohydrates such as cellulose and starch or other polymeric carbohydrates, or other organic polymers and any copolymers, composite materials or combination of the above inorganic or organic materials. Solid phases, as defined herein, may comprise functional groups, such as hydroxyl or amino groups or other functional groups known to those skilled in the art, which may or may not be protected.

The term "solid support" as used herein refers to a solid phase that is derivatized to comprise functional groups that are suitable to participate in the coupling reactions of an oligonucleotide synthesis. Solid phases, as defined herein, may comprise functional groups, such as hydroxyl or amino groups or other functional groups known to those skilled in the art, which may or may not be protected. The functional groups include, but are not limited to either unprotected, e.g. free hydroxyl groups, or protected hydroxyl groups that need to be deprotected prior to the coupling reaction. Suitable protecting groups include, but are not limited to dimethoxytrityl (DMT), methoxyethylidene, levulinyl and 9-fluorenylmethoxycarbonyl (Fmoc). The solid support is subjected to all of the reaction cycles involved in SPOS as discussed above, including, but not limited to cycles of deprotection reactions, coupling reactions with nucleotide synthons, including but not limited to phosphoramidite synthons, and other chemical reactions in a stepwise manner to build oligonucleotides on the surface of the solid phase, as described under the term "oligonucleotide synthesis" and in the references cited therein.

The term "solid support component" as used herein refers to solid support that is incorporated in a mixture of solid supports. Two or more solid supports that are physically mixed together to create a new solid support each constitute a solid support component of the new solid support.

The term "preloaded solid support" as used herein refers to a solid support that comprises a covalently attached nucleoside or oligonucleotide. The nucleoside or oligonucleotide of a preloaded support provides the functional group that is elongated in the course of an oligonucleotide synthesis. The covalently attached nucleoside or oligonucleotide determines the base composition at the end of the oligonucleotide to be synthesized, i.e. the sequence of the oligonucleotide at the terminal position. For example, a covalently attached nucleoside of a preloaded solid support that is employed in an oligonucleotide synthesis in 3' to 5' direction determines the 3' terminal nucleoside of the oligonucleotide. Certain preloaded solid supports are commercially available, e.g. nucleoside loaded CPG as depicted in the product brochures of Proligo LLC, Boulder, Colo., USA. In these commercially available preloaded supports, the nucleoside is protected with a standard protecting group, such as a DMT group at the 5'-position and the oligonucleotide synthesis is performed on the support in the 3' to 5' direction. Preloaded solid supports are generally limited in their use, because they can only be used to synthesize oligonucleotides with a predetermined end sequence. For example, a commercially available preloaded solid support with a covalently attached thymidine nucleoside can only be used to synthesize oligonucleotides that contain a thymidine nucleoside at their 3'-end.

The term "universal solid support" as used herein refers to a solid support that does not contain covalently attached nucleosides or oligonucleotides. In contrast to preloaded supports, universal supports can be employed to synthesize any oligonucleotide sequence without any sequence restrictions at the end of the oligonucleotide. With universal solid supports, the nucleotide synthon applied in the first coupling reaction of an oligonucleotide synthesis determines the sequence at the end of the synthesized oligonucleotide. For example, the first 5'-DMT protected nucleoside 3'-phosphoramidite employed in the synthesis of an oligonucleotide in 3' to 5' direction determines the 3'-nucleoside unit of the oligonucleotide.

As used herein the term "linker" refers to a bifunctional chemical moiety that covalently connects the solid phase of a solid support with the first nucleoside of the oligonucleotide to be synthesized in an oligonucleotide synthesis. A linker introduces a cleavage site that allows for the cleavage of the synthesized oligonucleotide from the solid support under suitable cleavage conditions. An example of a linker includes, but is not limited to the structure illustrated by Formula (1), below. Formula (1) depicts a preloaded solid support, as described in Beaucage and Iyer (1992) Tetrahedron 48:2223-2311. In Formula (1), the linker is comprised of a succinyl moiety, —C(=O)—CH$_2$—CH$_2$—C(=O)—, that covalently connects the solid phase LCAA CPG with the 3'-hydroxyl group of a nucleoside. LCAA CPG is a controlled pore glass with an organic coating comprised of primary amino groups. The succinyl linker is connected to the nucleoside by an ester group —C(=O)—O—, which represents the cleavage site. After the oligonucleotide is synthesized, it is cleaved from the solid support via hydrolysis of the ester group using standard methods, including but not limited to e.g. concentrated ammonia.

(1)

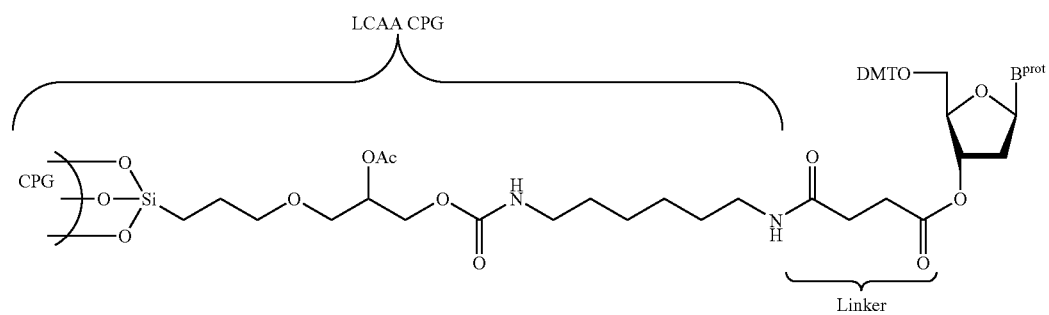

B$^{prot}$ = nucleobase, with protective group where applicable

The term "universal linker" as used herein refers to a linker of a universal solid support. A universal linker covalently connects the solid phase of the universal solid support with the first nucleotide synthon that is coupled to the support in the course of an oligonucleotide synthesis. An example of a universal linker includes, but is not limited to the structure illustrated by Formula (2), below. Formula (2) depicts a universal solid support described by Kumarev et al., WO 01/96357, which is incorporated herein by reference in its entirety. The linker illustrated in Formula (2), is comprised of an oxalyl moiety that is covalently attached to the 5'-hydroxyl group of a 2'/3'-monoacetylated inosine nucleoside. The universal linker covalently connects the solid phase aminopropylsilane CPG with the 3'-phosphate group of the first nucleotide synthon that is coupled to the universal solid support in the course of an oligonucleotide synthesis. The linker in Formula (2) introduces a cleavage site at the 3'-terminal phosphate group of the synthesized oligonucleotide. Under standard basic deprotection conditions, the 2'/3'-acetyl group of the inosine nucleoside is deprotected and the liberated hydroxyl group participates in an intramolecular reaction with a neighboring phosphate group to form a cyclic phosphotriester intermediate, which is further cleaved under basic conditions to produce a 2',3'-phosphodiester and a released 3'-OH oligonucleotide.

A representative example of orthogonal protective groups includes the combination of DMT and levulinyl protecting groups to protect hydroxyl groups. DMT protective groups are cleaved under mild acidic conditions, e.g. 3% trichloroacetic acid in dichloromethane for approximately 2 hours at room temperature. Levulinyl protective groups, on the other hand, are substantially stable under such mild acidic conditions as exemplified by Kumar et al. (1984) J. Org. Chem. 49:4905-4912. Levulinyl protective groups are cleaved with solutions of hydrazine in neutral organic buffers, e.g. 1 molar hydrazinium hydrate in a mixture of pyridine and acetic acid 3/2, v/v, for 5 minutes at room temperature. DMT protective groups are substantially stable under these deprotection conditions, see Kumar et al. (1984) J. Org. Chem. 49:4905-4912. Because each of the DMT and levulinyl protective groups on hydroxy functions can be removed selectively in the presence of the other group the DMT and the levulinyl groups are orthogonal protective groups as defined herein. There are many other examples of orthogonal protective groups that are known to those skilled in the art. A comprehensive overview on protective groups is provided in Wuts and Greene in *Protective Groups in Organic Synthesis*, Wiley-Interscience, ISBN 0471160199 (1999, 3$^{rd}$ edition) The present invention provides methods for the serial synthesis of two or more different oligonucleotides on the same solid support in one

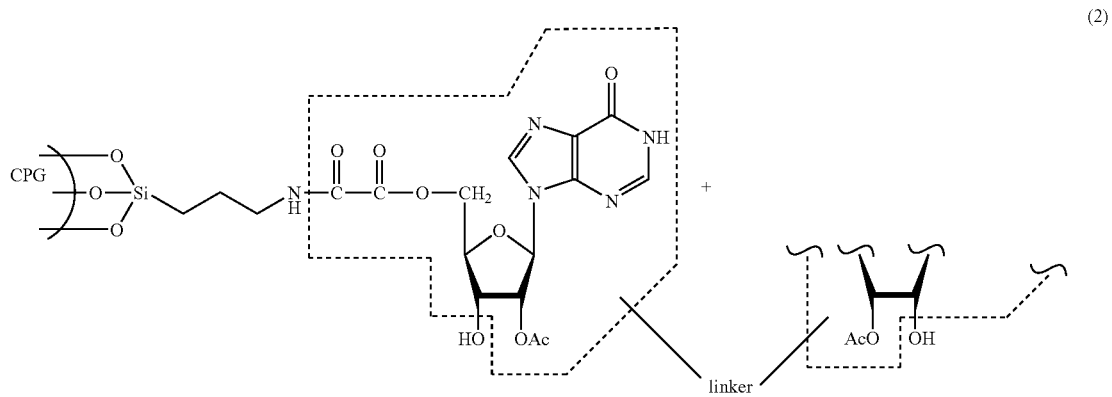

(2)

The term "anchor group" as used herein refers to a functional group to which the first nucleotide synthon is attached in the course of an oligonucleotide synthesis. Anchor groups include, but are not limited to functional groups, such as hydroxyl or amino groups or any other functional groups known to those skilled in the art, which may or may not be protected. In a preferred embodiment, the anchor group is a hydroxyl group, e.g. a 5'- or 3'-hydroxyl group of the nucleoside of a preloaded solid support, or a hydroxyl group of a universal solid support as described above.

The term "orthogonal protective groups" refers to two or more protective groups that can be removed selectively with respect to each other, i.e. the removal of each of the orthogonal protective groups can be performed without cleaving any other orthogonal protective group present. The orthogonal protective groups protect the anchor groups as defined above. As used herein, a "subset" refers to the portion of anchor groups protected by a particular orthogonal protective group, relative to all or the whole set of anchor groups. In one embodiment, the orthogonal protective groups are selected from the group including, but not limited to dimethoxytrityl (DMT), methoxyethylidene, levulinyl and 9-fluorenylmethoxycarbonyl (Fmoc).

synthetic run, also referred to herein as "tandem synthesis." Briefly, the method of the present invention comprises the steps of: a) providing a solid support, wherein said solid support is comprised of anchor groups that are protected by two or more orthogonal protective groups; b) removing one of said orthogonal protective group from the anchor groups; c) synthesizing an oligonucleotide on the deprotected anchor group; d) capping the synthesized oligonucleotide; e) repeating steps b) to d) until all of the orthogonal protective groups are deprotected, wherein step d) is omitted for the last orthogonal protective group; and f) cleaving all synthesized oligonucleotides from the solid support and subjecting them to conditions that are suitable to deprotect the oligonucleotides. Excellent coupling rates and yields are obtained using the method of this invention.

Figure 1:
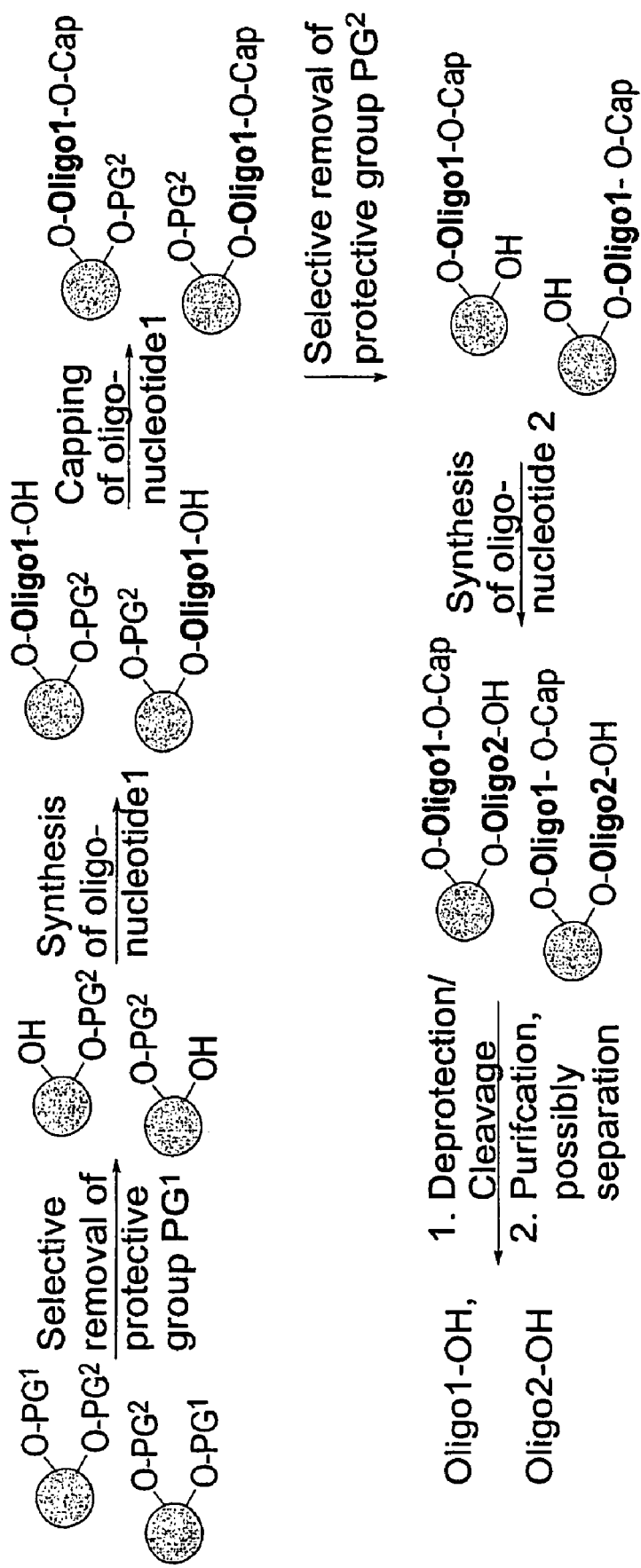
FIG. 1 is a schematic representation of a tandem oligonucleotide synthesis, which provides two oligonucleotides of differing sequence (oligo 1 and oligo 2) in a single synthetic run using a homogeneous solid support.
Figure 2:
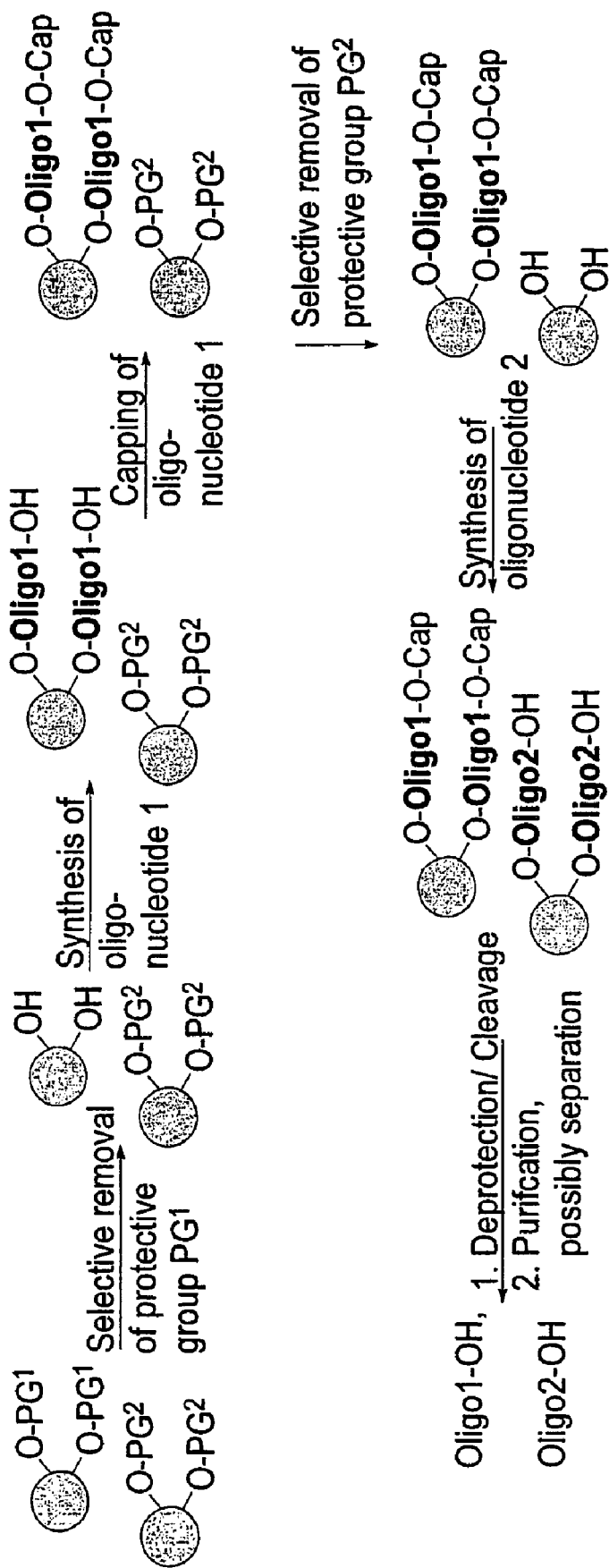
FIG. 2 is a schematic representation of a tandem oligonucleotide synthesis, which provides two oligonucleotides of differing sequence in a single synthetic run using a composite solid support.

The method of the present invention is based on orthogonally protected anchor groups situated on the solid support of the invention, each of which is successively used to synthesize one of the desired sequences, as outlined in FIGS. 1 and 2. As noted above, the term "orthogonal protective groups" refers to protective groups that can be removed selectively with respect to each other, i.e. the removal of each of the orthogonal protective groups can be performed without cleaving any other orthogonal protective group present.

Orthogonal protective groups can be selected from the group including, but are not limited to DMT, methoxyethylidene, levulinyl and Fmoc. A representative example of orthogonal protective groups includes, but is not limited to the combination of DMT and levulinyl protecting groups to protect hydroxyl groups. A comprehensive overview on protective groups is provided in Wuts and Greene in *Protective Groups in Organic Synthesis*, Wiley-Interscience, ISBN 0471160199 (1999, 3$^{rd}$ edition). Any protecting group that can be selectively removed in the presence of other protecting groups can be used in the method of this invention.

Subsequent to the selective removal of the first of the respective orthogonal protective groups, the first oligonucleotide is assembled on the deblocked anchor groups according to standard methods for the solid phase synthesis of oligonucleotides. The methods of this invention can be applied to any known methods for the solid phase synthesis of oligonucleotides, including but not limited to phosphoramidite chemistry, H-phosphonate chemistry, phosphotriester chemistry, or any other synthetic chemistry utilized to prepare oligonucleotides on solid supports. Furthermore, the methods of the invention can be adapted to universal linker systems, as well as, to those preloaded with the first nucleoside of the oligonucleotide to be synthesized. In a preferred embodiment, phosphoramidite chemistry is employed to synthesize the oligonucleotide. Following the capping of said first oligonucleotide, the anchor groups blocked by a second type of protective group are selectively liberated, which then serve as the starting point for the assembly of the second oligonucleotide, and so forth. After completion of all of the syntheses on the solid support, the synthesized oligonucleotides are further processed as a mixture during the release and deprotection steps. Preparations obtained using the method of this invention, generally contain a mixture of two or more oligonucleotides. They are particularly useful in applications that require pairs of oligonucleotide primers, several probes at a time, duplexed nucleic acid fragments and the like, including but not limited to PCR, sequencing, multiplexed genotyping, cloning and RNA interference.

The solid phase of the solid support can be an inorganic polymer, including, but not limited to inorganic oxides, such as silica, alumina, zeolites and controlled pore glass (CPG), a modified inorganic polymer, such as silica or CPG with an organic coating, e.g. aminopropyl-silane derivatized silica or aminopropyl-silane derivatized CPG, or an organic polymer, including, but not limited to polystyrene, polyacrylamide, polymethacrylate, polyvinylalcohol, or other synthetic polymers, carbohydrates, including but not limited to cellulose and starch or other polymeric carbohydrates, or other organic polymers and any copolymers, composite materials or combination of the above inorganic or organic materials. Solid phases, as defined herein, may comprise functional groups, such as hydroxyl or amino groups or other functional groups known to those skilled in the art, which may or may not be protected.

The methods disclosed herein are applicable to solid phase oligonucleotide synthetic schemes in which the growing oligonucleotide chain is assembled in the 3' to 5' direction, as well as, in solid phase oligonucleotide synthetic schemes in which the growing oligonucleotide chain is assembled in the 5' to 3' direction. The methods disclosed herein can be applied either with or without removing the final terminal protective group following the synthesis of the last assembled oligonucleotide. In the former case, all of the oligonucleotides synthesized are jointly processed through all work-up steps and transferred in combination to the final application. In the latter case, by utilizing the terminal protective group as a handle the last oligonucleotide synthesized may be separated, i.e. by employing the commonly used terminal dimethoxytrityl group as a handle in a simple, reversed-phase cartridge based purification step.

Included in the present invention are novel solid supports comprised of combinations of two or more orthogonal protective groups, as well as, methods for their preparation and their application in said tandem oligonucleotide synthesis. The solid supports disclosed herein enable the tandem synthesis of oligonucleotides on the same support without the need for reinitializing the set-up between each synthetic run, in particular exchanging the solid support container and re-programming the synthesizer. In addition, oligonucleotides synthesized on the same support by the methods of the invention in most instances can be subjected to joint work-up steps including cleavage, purification, desalting and concentration. Finally, they can be directly employed to most of the relevant ultimate applications, as their 3'- and 5'-hydroxyl groups are unmodified, particularly they do not carry phosphate groups.

The novel solid supports of this invention may be derivatized either with or without the first nucleoside of the oligonucleotide to be synthesized, as depicted in formulae (3) and (4), below.

Q-L-N-PG  (3)

Q-U-PG  (4)

wherein

Q is a solid phase as defined herein;

L is a linker as defined herein;

U is a universal linker as defined herein;

N is a nucleoside moiety establishing a terminal nucleoside of the oligonucleotide to be synthesized. In one embodiment, N is selected from the group including, but not limited to compounds illustrated by formulae (5) and (6), below.

wherein $R_1$ is selected from the group including, but not limited to —H, —OH, —F, an optionally substituted alkoxyl or alkenoxyl group having from 1 to 4 carbon atoms, including, but not limited to the groups —OCH$_3$, —OCH$_2$CH=CH$_2$ or —OCH$_2$OCH$_2$CH$_2$OCH$_3$, a protected amino group, or OR$_2$ wherein R$_2$ represents a protective group useful in oligoribonucleotide synthesis, including, but not limited to the tert-butyldimethylsilyl group, or any other protective group useful for the protection of the 2'-OH function of ribonucleosides known to those skilled in the art;

B is a nucleobase, selected from the group including, but not limited to adenine, cytosine, guanine, thymine and uracil, or a chemically modified derivative thereof, the exocyclic amino groups of the nucleobase may bear a protective group useful in oligonucleotide synthesis, as exemplified by the protective groups including, but not limited to the benzoyl protective group for adenine and cytosine, the isobutyryl protective group for guanine, tert-butylphenoxyacetyl (TAC) protective groups for adenine, cytosine and guanine, and any other protective group for nucleobases known to those skilled in the art;

X and Y are independently selected from —O or —NH, X represents the anchor group of the solid support and Y represents the site of attachment to the linker on the solid phase; and PG is selected from H or a protective group.

In one embodiment, the solid supports comprising universal linkers according to the general formula (4) above, are selected from the group of compounds illustrated by formula (7):

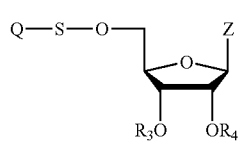

(7)

wherein

Q is a solid phase as defined herein;

S is a bifunctional spacer moiety that covalently connects the solid phase with the 5'-hydroxyl group of the depicted furane ring; examples of S include, but are not limited to —C(=O)—, diacyl moieties, selected from the group including, but not limited to oxalyl, malonyl, succinyl, glutaryl and so forth, alkylidene moieties, including, but not limited to methylidene, ethylidene, propylidene and so forth, alkylacyl moieties, including but not limited to —C(=O)—CH$_2$—, —CH$_2$—C(=O)—, —C(=O)—CH$_2$—CH$_2$—, —CH$_2$—CH$_2$—C(=O)— and so forth, phosphate moieties including, but not limited to —P(=O)(OH)— and protected phosphate moieties including, but not limited to —P(=O)(OR$_5$)—, wherein R$_5$ is selected from the group consisting of phosphate protective groups known to those of skill in the art, including but not limited to 2-cyanoethyl;

Z is a nucleobase, selected from the group including, but not limited to adenine, cytosine, guanine, thymine or uracil, or a chemically modified derivative thereof, the exocyclic amino groups of the nucleobase may bear a protective group useful in oligonucleotide synthesis, as exemplified by the protective groups including, but not limited to the benzoyl protective group for adenine and cytosine, the isobutyryl protective group for guanine, tert-butylphenoxyacetyl (TAC) protective groups for adenine, cytosine and guanine, and any other protective group for nucleobases known to those skilled in the art, or is H, —OMe, hypoxanthine or any other moiety that is compatible with both the functionality of an universal linker, as defined above, and all the steps-involved in SPOS;

R$_3$ and R$_4$ are protective groups blocking the 2- and the 3-hydroxyl group of the depicted furan ring, respectively; either of said 2- or 3-hydroxyl groups functions as an anchor group, as described above; R$_3$ and R$_4$ are selected from the group including, but not limited to the following combinations of substituents: R$_3$ is H and R$_4$ is a standard capping group including, but not limited to —COCH$_3$, or vice versa; or R$_3$ is a standard protective group and R$_4$ is a capping group including, but not limited —COCH$_3$, or vice versa; or R$_3$ and R$_4$ together represent a methoxyethylidene moiety that bridges the oxygens at positions 2 and 3 of the furan ring.

Use of a solid support derivatized as depicted by general formula (3) requires that the instrument used in the tandem synthesis be programmed to reflect that the first nucleoside of the oligonucleotide sequence is already attached to the solid support. Derivatization of the solid support as depicted by general formula (4) requires that the instrument be programmed to reflect that the first nucleoside of the oligonucleotide sequence is introduced in the first coupling step.

The solid supports of the present invention are comprised of anchor groups with two or more orthogonal protective groups on the same support. The number of orthogonal protective groups required for each oligonucleotide synthesis is determined by the number of oligonucleotides to be tandemly synthesized. In general, if m oligonucleotides are to be prepared in one synthetic run, then m orthogonal protective groups are needed. Optionally, one of the anchor groups may be unprotected. In this case, the unprotected anchor group serves as the starting point of the first oligonucleotide to be synthesized in the tandem synthesis and m−1 orthogonal protective groups are sufficient for the tandem preparation of m oligonucleotides. In this embodiment the method of the invention comprises the steps of: a) providing a solid support, wherein said solid support is comprised of anchor groups that are partially unprotected, the remainder of the anchor groups being protected by one or more protective groups, the protective groups being orthogonal to each other in case more than one protective group is employed; b) synthesizing an oligonucleotide on the unprotected anchor groups; c) capping the synthesized oligonucleotide; d) removing one protective group from the anchor groups; e) synthesizing an oligonucleotide on the deprotected anchor groups; f) repeating steps c) to e) until all of the orthogonal protective groups are deprotected; and g) cleaving all synthesized oligonucleotides from the support.

According to the method of the present invention, different types of derivatizations of the solid support may be arbitrarily combined to conduct the intended tandem synthesis. For example, two or more derivatizations as described in formula (3) comprising two or more different orthogonal protective groups may be applied. Alternatively, two or more derivatizations as described in formula (4) may be applied with two or more different orthogonal protective groups. Furthermore, the types of derivatization described in formula (3) and formula (4) may also be mixed in one tandem synthesis if they comprise different orthogonal protective groups.

In one embodiment of the invention, the solid support is homogeneously derivatized with two or more orthogonal protective groups referred to herein as a "homogeneous solid support." Two more different oligonucleotides can be synthesized on this type of support, depending on the number of orthogonal protective groups employed. FIG. 1 illustrates the use of a homogeneous solid support derivatized with two orthogonal protective groups (PG$^1$ and PG$^2$) in the tandem synthesis of two oligonucleotides (Oligo1 and Oligo2). With reference to FIG. 1, in the first step of the synthesis, the protective group PG$^1$ is selectively removed, resulting in a homogeneous distribution of unprotected anchor groups, i.e. free hydroxyl groups, and protected (PG$^2$) anchor groups on the support. In the following steps, the first oligonucleotide (Oligo1) is assembled on the support via conventional solid phase oligonucleotide synthesis, e.g. phosphoramidite synthesis. After the assembly of Oligo1, the support is capped with a conventional capping reagent to prevent all Oligo1 sequences from being further elongated in the tandem synthesis. In the next step, the protective group PG$^2$ is removed selectively, resulting in a homogeneous distribution of unprotected anchor groups, i.e. free hydroxyl groups, and capped Oligo1 on the support. In the following steps, the second oligonucleotide (Oligo2) is assembled on the support via conventional solid phase oligonucleotide synthesis, e.g. phosphoramidite synthesis. After the assembly of Oligo2, both Oligo1 and Oligo2 are cleaved from the support and deprotected to provide a mixture of the two oligonucleotides. The mixture of oligonucleotides is further processed in accordance with the intended application of the oligonucleotides, e.g. by desalting, or by chromatographic purification etc.

Homogeneous solid supports can be prepared using a number of methods. In one embodiment, the homogeneous solid supports are prepared in a stepwise manner, starting with a solid phase that comprises unprotected anchor groups. The unprotected anchor groups are reacted with a first orthogonal protective group (e.g., $PG^1$) to the desired extent by addition of the respective reagents that introduce the protective group in the appropriate amounts (e.g. in a ratio of 1:2 reagent: anchor groups, if protection of one half of the anchor groups is desired). After the initial derivatization with the first orthogonal protective group the remaining free anchor groups are reacted with a second orthogonal protective group (e.g., $PG^2$) in a corresponding manner with a second reagent that introduces the second orthogonal protective group. This reaction scheme can be repeated, with the addition of more orthogonal protective groups until virtually all anchor groups are protected and all desired orthogonal protective groups are introduced. This method is particularly useful if two types of orthogonally protected anchor groups, or if one type of protected anchor group in combination with unprotected anchor groups, is desired. In the latter case, only one derivatization of approximately 50% of the anchor groups is performed. The remaining unreacted anchor groups may or may not be converted into orthogonally protected anchor groups by applying an excess of the appropriate reagent to introduce the second protective group.

In another embodiment, the homogeneous solid support for a tandem synthesis is prepared by the simultaneous application of two or more reagents, which introduce the orthogonal protective groups. For example, a mixture of O3'-succinate-(4-nitrophenyl)ester nucleosides with different orthogonal O5'-protective groups could be employed in a loading reaction on amino-functionalized solid phases to generate a homogeneous preloaded support.

In another one embodiment of the present invention, the solid support is generated by mixing two or more solid support components, wherein the anchor groups of each solid support component, is uniformly protected by a unique orthogonal protective group. Solid supports that are generated from two or more solid support components are referred to herein as "composite solid supports." FIG. 2 illustrates the use of a composite solid support derivatized with two orthogonal protective groups ($PG^1$ and $PG^2$) in the tandem synthesis of two oligonucleotides (Oligo1 and Oligo2). With reference to FIG. 2, in the first step of the synthesis, the protective group $PG^1$ is selectively removed, resulting in a composite support that consists of a solid support component with unprotected anchor groups, i.e. free hydroxyl groups, and a solid support component with protected ($PG^2$) anchor groups on the support. In the following steps, the first oligonucleotide (Oligo1) is assembled via conventional solid phase oligonucleotide synthesis, e.g. phosphoramidite synthesis. After the assembly of Oligo1 the composite support is capped with a conventional capping reagent to prevent all Oligo1 sequences from being further elongated in the tandem synthesis. In the next step, the protective group $PG^2$ is removed selectively, resulting in a composite solid support that consists of a solid support component with unprotected anchor groups, i.e. free hydroxyl groups, and a solid support component with attached capped Oligo1. In the following steps, the second oligonucleotide (Oligo2) is assembled via conventional solid phase oligonucleotide synthesis, e.g. phosphoramidite synthesis. After the assembly of Oligo2, both Oligo1 and Oligo2 are cleaved from the composite support and deprotected to provide a mixture of both oligonucleotides. The mixture of oligonucleotides is further processed in accordance with the intended application of the oligonucleotides, e.g. by desalting, or by chromatographic purification etc. Two more different oligonucleotides can be synthesized on a component solid support, depending on the number of solid support components, which contain other orthogonal protective groups.

Each solid support component of a composite solid support is easily prepared in separate reactions through methods well known in the art. One method to prepare such solid support components consists of introducing the orthogonal protective groups onto unprotected anchor groups. For example, a dimethoxytrityl protective group can be introduced to the hydroxyl groups of a solid support component in a tritylation reaction, as described by Reddy et al. (1987) Tetrahedron Letters 28:23-26, which is incorporated herein by reference in its entirety. In another example, a tert-butyldimethylsilyl protective group is reacted with the hydroxyl groups of a solid support component in a silylation reaction. Another method to prepare solid support components is based on the use of loading reagents that already contain protected anchor groups. For example, a dimethoxytrityl protected nucleoside loading reagent, e.g. an O5'-dimethoxytrityl-O3'-succinate-(4-nitrophenyl)ester of a nucleoside, as described by Caruthers et al. (1982) in *Chemical and Enzymatic Synthesis of Gene Fragments, A Laboratory Manual*, Verlag Chemie, Gassen and Lang, eds. ISBN 3-527-26063-3, can be employed to prepare a preloaded solid support component with dimethoxytrityl protected anchor groups from amino-functionalized solid phases. Analogously, a levulinyl protected nucleoside loading reagent, e.g. a O5'-levulinyl-O3'-succinate-(4-nitrophenyl)ester of a nucleoside, can be employed to prepare a preloaded solid support component with levulinyl protected anchor groups from amino-functionalized solid phases.

Component supports are mixed according to their loading in a ratio that reflects the intended ratio of the oligonucleotides to be prepared in the tandem synthesis. It may be advantageous to apply an excess of a support component in case a partial loss of the protective group of the component is anticipated during the tandem synthetic run. For example, if 9-fluorenylmethyloxycarbonyl (Fmoc) is used as one of the orthogonal protective groups, it is advantageous to apply a 20 to 40% excess of the corresponding Fmoc solid support component, in order to compensate for the partial loss of Fmoc-groups during the course of the tandem synthesis. The extent of the loss of Fmoc-protection, as well as, the optimal amounts of said excess, will primarily depend on the size and the number of oligonucleotides synthesized prior to the deblocking of the Fmoc-protected anchor group.

As noted above, the examples depicted in FIGS. 1 and 2 can be extended to the synthesis of more than two oligonucleotides by either increasing the number of orthogonal protective groups on the homogeneous support or by adding more solid support components that contain other orthogonal protective groups to the composite solid support. The sequence of synthetic steps is extended to include additional capping, synthesis and deprotection steps in this case in order to accommodate the serial synthesis of the added oligonucleotides in accordance with FIG. 1 or 2.

A preferred orthogonal protecting group for tandem oligonucleotide synthesis is the dimethoxytrityl (DMT) group, which is removed during the standard synthetic cycle of phosphoramidite mediated oligonucleotide synthesis and therefore, will be the first of the orthogonal protective groups on the solid support to be removed in a tandem oligonucleotide synthesis. The DMT group is introduced using a simple tritylation process, and as noted above, it is removed during the course of the first step of automated SPOS, simultaneously allowing the progression of the detritylation to be monitored and the loading of DMT protected anchor groups to be determined via VIS-spectroscopy. The methoxyethylidene protective group on the 2'/3'-diol function of the ribonucleoside portion of a universal linker, as described above, is also preferred as an orthogonal protective group. The methoxyethylidene protective group is cleaved during the first acidic reaction step in a phosphoramidite mediated synthesis to generate a 2'/3'-monoacetate with one free hydroxyl group. Alternatively, unprotected anchor groups may be used in conjunction with one or more orthogonal protective groups. For example, free hydroxyl groups can be employed together with one or more orthogonal protective groups. In this case, the free hydroxyl groups represent the starting point of the tandem oligonucleotide synthesis.

Examples of protective groups, that are orthogonal to a DMT-group, or to a methoxyethylidene group on the 2'/3'-cis diol function of a universal linker as described above, or to an unprotected anchor group include, but are not limited to, the 9-fluorenylmethyloxycarbonyl (Fmoc) protective group, which can be removed under mildly basic conditions, the 4-oxopentanoyl (levulinyl) protective group, which can be removed under neutral conditions with a solution of hydrazine hydrate in a pyridine/acetic acid buffer, and trialkylsilyl protective groups, which can be removed with deprotection solutions that contain fluoride ions. The choice of orthogonal protective groups that can be used in a tandem oligonucleotide synthesis as described herein is not limited to the examples mentioned above. Any other protective group that is an orthogonal protective group as defined herein can be employed in the method of this invention. All orthogonal protective groups employed in the same synthesis, however, must be stable under the conditions of the oligonucleotide assembly chemistry.

Additional applications of the described homogeneous solid supports are included within the scope of this invention. For example, bead preparations with two or more different oligonucleotides homogeneously tethered to all beads may be prepared as described with linkers that are stable under the conditions of the deprotection of the synthesized oligonucleotides. Such bead preparations are useful in hybridization assays. Linkers used for such purposes are potentially simpler compared to linkers that are cleavable under the conditions of deprotection of the synthesized oligonucleotides.

Figure 3:
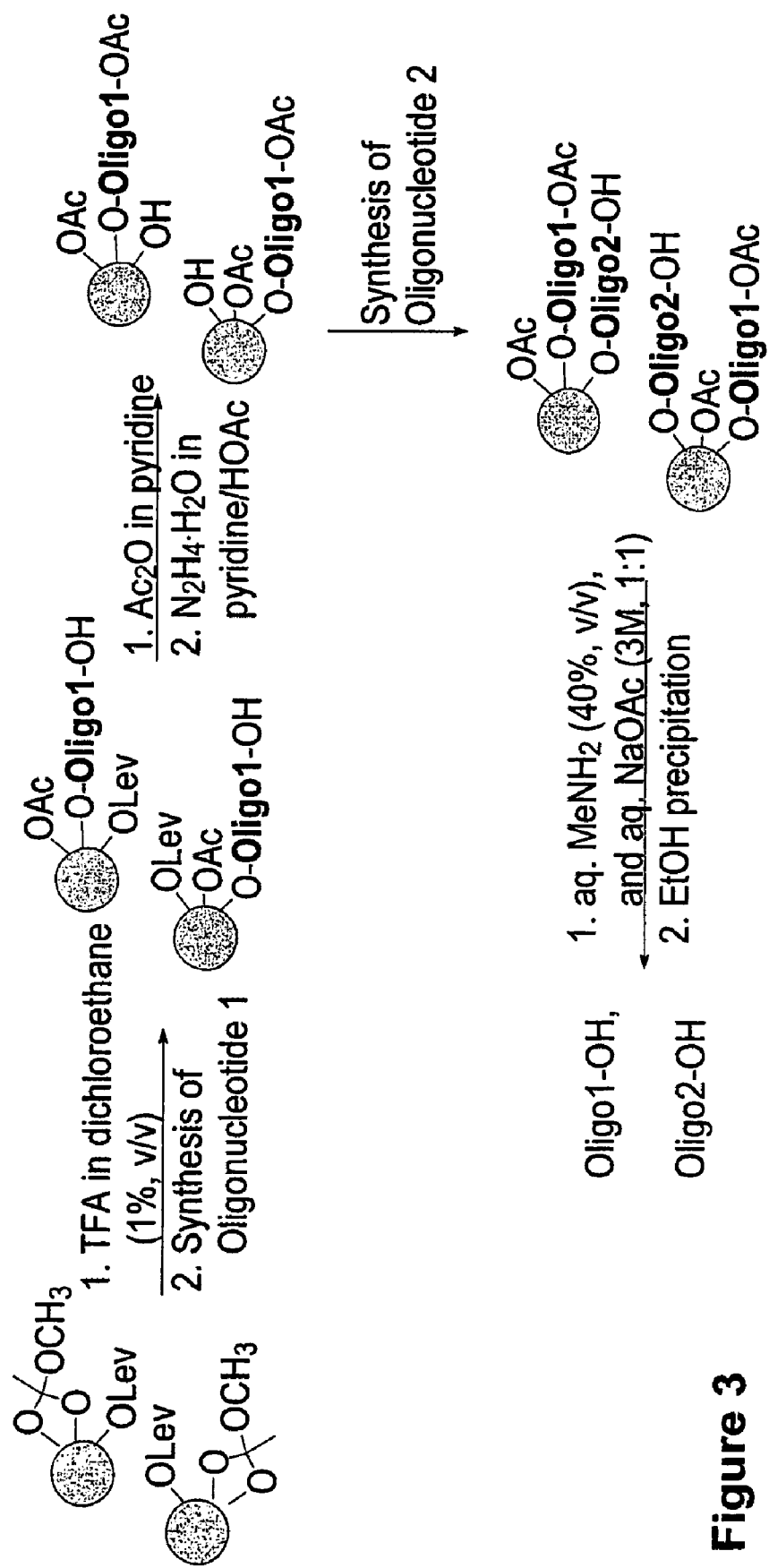
FIG. 3 is a schematic representation of a tandem oligonucleotide synthesis employing a homogeneous solid support, comprising anchor groups that are protected by O2',O3'-methoxyethylidene moieties, and anchor groups that are protected by levulinyl protective groups.

FIG. 3 illustrates the use of a homogeneous solid support, derivatized with universal linkers, in the tandem synthesis of two oligonucleotides using standard protocols for phosphoramidite chemistry. With reference to FIG. 3, equal shares of the hydroxyl anchor groups on the solid support are protected either with 2'/3'-O/O-methoxyethylidene groups ($OCH_3$) or with levulinyl groups (Olev). During the first step of the chain extension cycle, the 2'/3'-O/O-methoxyethylidene protecting group is selectively opened to one side yielding an acetylated and a free hydroxyl group, overall resulting in a homogeneous 1:1-distribution of free and levulinyl protected hydroxyl groups on the support. In the following steps the first oligonucleotide (Oligo1) is assembled on the support via conventional solid phase oligonucleotide synthesis. The next two steps differ from standard protocols, first regarding the order of the steps and second regarding the reagents used, but still can be performed on an automated synthesizer. In the first of these two steps, Oligo1 is capped with an acetyl group to prevent its further elongation by subjecting the support to conventional capping reagents, as used in the capping steps of standard SPOS. In the second of these two steps, the levulinyl group is removed selectively by briefly treating with a solution of hydrazine in a pyridine/acetic acid buffer, resulting in a homogeneous distribution of free hydroxyl groups and capped Oligo1 on the support. In the following steps, the second oligonucleotide (Oligo2) is conventionally assembled on the liberated hydroxyl groups. Following the synthesis of Oligo2, the support is subjected to standard deprotection/cleavage conditions affording a mixture of both oligonucleotides that is worked up, e.g. by a desalting step.

Figure 4:
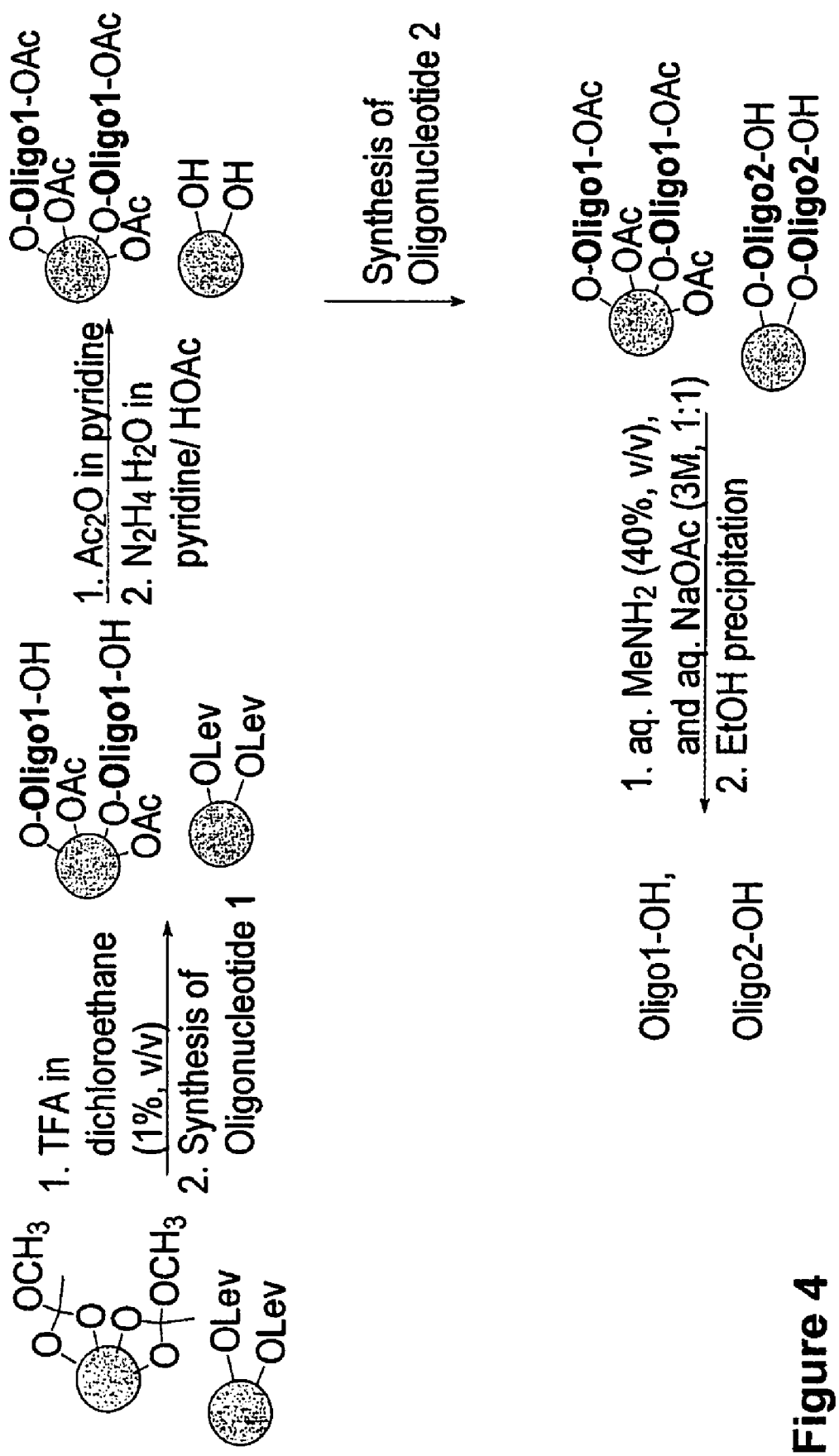
FIG. 4 is a schematic representation of a tandem oligonucleotide synthesis employing a composite solid support, comprising anchor groups that are protected by O2',O3'-methoxyethyline moieties, and anchor groups that are protected by levulinyl protective groups.

FIG. 4 illustrates the use of a composite solid support derivatized with universal linkers in the tandem synthesis of two oligonucleotides using standard protocols for phosphoramidite chemistry. With reference to FIG. 4, the composite support consists of equal amounts of two solid support components having the same loadings of hydroxyl anchor groups protected with 2'/3'-O/O-methoxyethylidene groups ($OCH_3$) or with levulinyl groups (Olev). During the first step of the chain extension cycle, the 2'/3'-O/O-methoxyethylidene protecting group is selectively opened to one side yielding an acetylated and a free hydroxyl group. Thus, overall a composite solid support consisting of one solid support component with free hydroxyl groups and a second solid support component with levulinyl protected hydroxyl groups is obtained. In the following steps, the first oligonucleotide (Oligo1) is assembled on the support via conventional solid phase oligonucleotide synthesis. The subsequent two steps differ from standard protocols in the same manner as noted above with respect to the example illustrated in FIG. 3. In the first of these two steps Oligo1 is capped with an acetyl group to prevent its further elongation by subjecting the support to conventional capping reagents, as used in the capping steps of standard protocols. In the second to these two steps, the levulinyl group is removed selectively by briefly treating with a solution of hydrazine in a pyridine/acetic acid buffer, resulting in a solid support that consists of a solid support component with free hydroxyl groups and a solid support component bearing capped Oligo1. In the following steps, the second oligonucleotide (Oligo2) is conventionally assembled on the liberated hydroxyl groups. Following the synthesis of Oligo2, the support is subjected to standard deprotection/cleavage conditions affording a mixture of both oligonucleotides that is finally worked up, e.g. by a desalting step. As noted above with respect to the example illustrated in FIG. 3, due to the simple and generally applicable synthetic process described in the invention, all of these steps all of these steps can be performed on an automated synthesizer.

In one embodiment of the invention, the last terminal protective group is removed during the synthesis of the last assembled oligonucleotides, i.e. the synthesis is performed in the DMT-off mode, resulting, subsequent to the cleavage/removal step, in a mixture of completely deprotected oligonucleotides. This crude product can be used as such or can be subjected to further, preferably collective work-up steps, e.g. desalting and/or concentration under reduced pressure, as described for example in Fischer et al. (1990) BioTechniques 9:300-301 and the Pharmacia Biotech NAP™-25 Column Instructions, each of which is specifically incorporated herein by reference in its entirety. Thus, e.g., a single ultrafiltration run or a precipitation step is sufficient to generate a mixture of oligonucleotides, such as primer pairs, that can be directly admitted to the final application. Optionally, further purification steps as known in art, e.g., gel electrophoreses, RP- or IE-BPLC, can be performed, giving rise to either individual or combined preparations of purified oligonucleotides.

According to yet another embodiment of the invention, said final terminal protective group is retained, i.e. the synthesis is performed in the DMT-on mode, resulting, subsequent to the cleavage/removal step, in a mixture of oligonucleotides of which one or more are completely deprotected and one is still bound to the terminal protective group, commonly a dimethoxytrityl-group. This terminal protective group can then be utilized as a handle in an additional purification step on a hydrophobic stationary phase, e.g. by passing through a reverse phase cartridge, allowing for the simple separation of the last synthesized oligonucleotides from the remaining ones. Finally, said terminal protective group is removed during or after the additional purification step, as described for example in Johnson et al. (1990) BioTechniques 8:424-428 and McBride et al. (1988) BioTechniques 6:362-367, each of which is specifically incorporated herein by reference in its entirety. In this manner, two discrete oligonucleotide preparations can be obtained from a single SPOS run, e.g. two fractions containing one oligonucleotide each are accessible by one tandem synthesis of two oligonucleotides; or one oligonucleotide can be singled out of a three-membered tandem synthesis leaving behind a composition of two oligonucleotides, such as a primer pair.

The novel methods and support preparations of this invention have significant advantages and do not suffer from the limitations inherent in the prior art methods. The solid supports described herein provide for a simple, smooth and efficient synthesis of two or more oligonucleotides of consistent quality that are useful for a broad range of applications. The methods of this invention are especially targeted to the cost effective production of oligonucleotides for applications employing two or more primers, probes, duplex nucleic acid fragments or the like. The methods of this invention can easily be adopted in syntheses of modified oligonucleotides, such as phosphorothioates, RNA derivatives and locked nucleic acids (LNA), and oligonucleotides conjugated to e.g. one or several dyes via a linker unit.

Example 1 describes the synthesis of universal solid support 8. The CPG-based universal solid support 8, which bears a protected anchor group, is prepared using the method described by Kumarev et al., WO 01/96357. The O2'/O3'-methoxyethylidene moiety of 8 is transferred to either the 2'-hydroxyl/3'-acetate or the 2'-acetate/3'-hydroxyl-derivative 9 upon a brief acidic treatment, e.g. with 1% trifluoroacetic acid in dichloroethane for 1 minute at room temperature, as illustrated in Scheme 1, below. Solid support 9 is well suited as a solid support component for the assembly of the first oligonucleotide in the course of a tandem synthesis. The same is true for the CPG derivative 10, which carries DMT-protected anchor groups. Compound 10 is obtained from compound 9 via by a simple tritylation procedure, as described in Example 2.

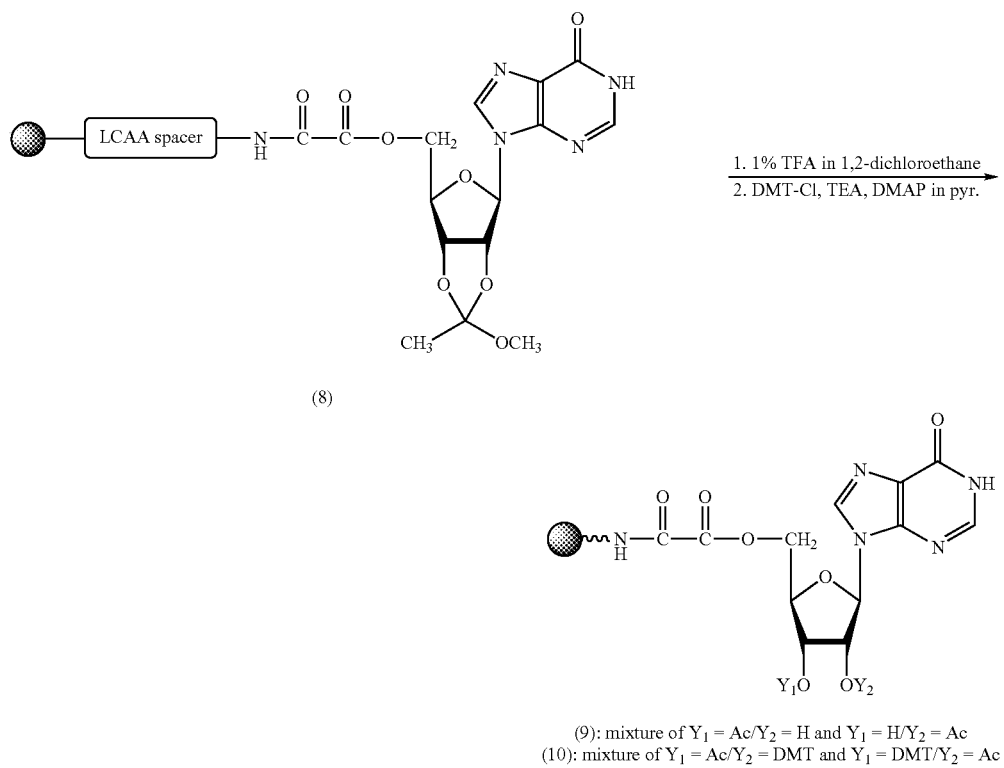

Due to their stability under the conditions involved in the cycles of an oligonucleotide synthesis, the Fmoc-group and the levulinyl protecting groups are useful as orthogonal protective groups in the context of a tandem oligonucleotide synthesis. The synthesis of corresponding CPG supports (11) and (12) is outlined in Scheme 2 and described in Examples 3 and 4. The solid supports (11) and (12) are well suited as solid support components in a tandem oligonucleotide synthesis. As an example, they can be combined with the solid support (9) in an appropriate ratio to provide a composite solid support that allows the synthesis of a first oligonucleotide on the solid support component (9) and the synthesis of a second oligonucleotide on a solid support component (11) or (12).

Scheme 2

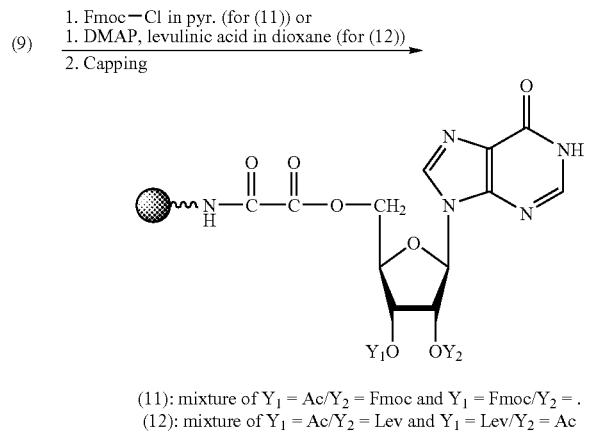

(11): mixture of $Y_1$ = Ac/$Y_2$ = Fmoc and $Y_1$ = Fmoc/$Y_2$ = .
(12): mixture of $Y_1$ = Ac/$Y_2$ = Lev and $Y_1$ = Lev/$Y_2$ = Ac In a preferred embodiment of the invention, solid support components (11) or (12) are applied in a mixture with the solid support components (8) or (10) for the synthesis of two oligonucleotides, to provide a composite support comprised of solid support components (8) or (10) and (11) or (12), respectively. A general procedure for such a tandem oligonucleotide synthesis, including the steps of removing the Fmoc- or the levulinyl group prior to the assembly of a second oligonucleotide is provided in Example 5. More specific examples of the tandem synthesis of oligonucleotides using the general procedure provided in Example 5 are described in Examples 6 to 9, 11 and 12.

Example 6 illustrates the tandem synthesis of three oligodeoxynucleotide primer pairs, having lengths of 8 to 15 bases, according to the general procedure described in Example 5 using composite solid supports derived from the solid support components (8) and (12). All of the oligonucleotide products were characterized by RP-HPLC and gel electrophoresis. The results of the gel electrophoresis are set forth in FIG. 5. Lanes 1, 2 and 3 represent primer pairs 1, 2 and 3, respectively.

Example 7 describes the synthesis of a sequencing primer pair consisting of a 23mer and 25mer oligodeoxynucleotide according to the general procedure described in Example 5 using composite solid support derived from the solid support components (8) and (12). The synthesized products were analyzed and their identity was verified both by comparing their HPLC retention times with those of the corresponding oligonucleotides prepared individually using standard means and by MALDI-TOF mass spectroscopic analysis. The results of the electrophoretic analysis are set forth in FIG. 6. Lanes 4 and 5 depict the separation of the two tandemly synthesized oligonucleotides. Lanes 1 and 2 represent the 23mer and 25mer, respectively, which were individually synthesized by conventional means, and lane 3 represents the separation of a mixture thereof. The same sequencing primer pair was also obtained according to procedures specified in Example 10, which are based on tandem synthesis using a homogeneous solid support.

Example 8 describes PCR experiments using primer pairs synthesized by the method described in Example 5. The two primer pairs were prepared employing the component solid supports (8) and (12). Reference oligonucleotide primers were individually synthesized. All PCR experiments were performed under three different sets of conditions. The resulting PCR products were analyzed by electrophoresis under non-denaturing conditions. The results are set forth in FIG. 7. With reference to FIG. 7, the upper set of gels depicts the results for primer pair #1 applying the three different PCR conditions C, D and E: lanes 1 to 4 represent to the primer pair obtained via a tandem oligonucleotide synthesis, lanes 5 represent the primer pair as obtained through conventional SPOS protocols in separate synthesis for each primer and lanes M contain size markers (50 bp ladder). The lower set of gels depicts the results for the primer pair #2 accordingly. As demonstrated in FIG. 7, the PCR products obtained from the tandem primers were identical with those generated with the reference primers in all cases and were of comparable quality.

Example 9 describes the preparation of a ternary composite solid support comprising the methoxyethylidene-modified universal CPG (10), the Fmoc-protected universal CPG (11), and the levulinyl-protected universal CPG (12) as support components. In addition, the use of this composite support for the tandem synthesis of three oligonucleotides $d(T)_9$, $d(T)_{12}$ and $d(T)_{15}$ in a ratio of approximately 1:1:1 is described. These three components of the crude product mixture were identified and characterized by anion-exchange HPLC, as depicted in FIG. 8.

In another preferred embodiment of the present invention, the loading of the Fmoc-protected CPG support (11) or the levulinyl protected CPG support (12) is adjusted to approximately 50% of the available hydroxy groups. The resulting support is a homogeneous solid support useful for a tandem oligonucleotide synthesis, as described in Example 10. It contains approximately 50% unprotected hydroxyl groups, which can be used in the synthesis of the first oligonucleotide of a tandem oligonucleotide synthesis and approximately 50% Fmoc- or levulinyl protected hydroxyl groups, which can be used in the synthesis of a second oligonucleotide on the same support in the tandem oligonucleotide synthesis. The ratio of Fmoc- or levulinyl protected and unprotected hydroxyl groups can be adjusted in this embodiment through the stoichiometry of the reagents applied to introduce the Fmoc- or levulinyl protective groups. The adjustment of the ratio of protected to unprotected hydroxyl groups is necessary in a case in which differential amounts of the two oligonucleotides to be synthesized are required. For example, a ratio of approximately 33% protected hydroxyl groups and approximately 66% unprotected hydroxyl groups can be employed to generate the two oligonucleotides in a molar ratio of approximately 1:2. Protocols for the preparation, as well as, the use in tandem synthesis of such a homogeneous solid support are described in Example 10. This example illustrates the preparation of a homogeneous support comprised of unprotected hydroxyl groups and those protected by levulinyl groups in a ratio of approximately 1:1.

The usefulness of preparative gel electrophoresis to jointly purify a tandem synthesized pair of oligonucleotide primers in one step is demonstrated in Example 11. The results are set forth in FIG. 9. The chromatograms represent the analyses before (FIG. 9A) and after (FIG. 9B) the purification. As can be seen from the corresponding HPLC chromatograms displayed in FIG. 9, the crude mixture is converted into a preparation of the primer pair that contains both oligonucleotides in almost equal amounts and high purity.

Example 12 describes the tandem syntheses of two oligonucleotide pairs, each of which are composed of two single-stranded complementary oligonucleotides that are able to form a duplexed oligonucleotide by hybridizing to each other. The actual existence of the double-stranded species and the complete conversion of its single stranded components were proven by non-denaturing gel electrophoresis, as depicted in FIG. 10. Lanes 1 and 2 represent a 40mer oligonucleotide marker. Lanes 3 to 5 and 6 to 8 illustrate the duplexes formed by oligonucleotide pairs 1 and 2, respectively.

The following examples are provided for illustrative purposes only and are not intended to limit the scope of the invention.

EXAMPLES

Example 1

Preparation of Universal Solid Support (8)

Dried long-chain-alkyl-amino (LCAA)-derivatized aminopropyl CPG (300 g, porosity 500 or 1000 Å, loading value for amine functions: 100 μmol/g, +/−20%) was suspended in 1000 mL oxalyl chloride at room temperature in a rotavap at high speed under reduced pressure for 20 minutes. The temperature was then raised to 100° C. and the excess oxalyl chloride was removed by distillation, requiring a period of about 3 hours. Following removal of the excess oxalyl chloride, a freshly prepared solution of O2',O3'-methoxyethylidene inosine (62 mmol, 2 equiv.) in anhydrous pyridine (1200 mL) and N-methylimidazole (10%, v/v) was added to the activated CPG and reacted at room temperature with high speed rotation under reduced pressure for 20 minutes, such that evaporation occurred. Acetic anhydride (120 mL) was then added to the reaction mixture over a period of 5 minutes at room temperature with intense agitation to provide CPG preparation (8). Following this final capping step, the product was collected on a glass-fritted funnel, washed several times with pyridine followed by acetonitrile, dried in vacuo and stored at 4° C.

CPG preparation (8) was calculated as having a loading value of 49 μmol/g, by cleaving off the inosine moieties in a test sample (aq. LiOH (1 M), stirring for 10 minutes at room temperature), and photometrical quantification at 254 nm.

Example 2

Preparation of the 2'/3'-DMT-protected Universal Solid Support (10)

The derivatized CPG (8), prepared as described in Example 1, was transferred to a glass-fritted funnel and washed once with a solution of TFA in 1,2-dichloroethane (1%, v/v), and successively with 1,2-dichloroethane and acetonitrile (3× each), to provide CPG preparation (9), which was dried in vacuo for 1 hour. To a portion of (9) with a total inosine loading of 34 μmol, was added a solution of dimethoxytrityl chloride (2.5 mmol, 74 eq.), DMAP (0.31 mmol) and triethylamine (2.92 mmol) in anhydrous pyridine (10 mL). The reaction mixture was stirred at room temperature for 2 hours. The resulting CPG was collected on a glass-fritted funnel, washed successively with pyridine (4×), acetonitrile (3×) and diethyl ether (1×), and finally dried in vacuo to afford the tritylated support (10).

For (10) a loading value of 53 μmol/g was measured by cleaving off the DMT moieties in a test sample (TFA (1%, v/v) in 1,2-dichloroethane), which were then quantified at 498 nm.

Example 3

Preparation of the 2'/3'-Fmoc-Protected Universal Solid Support (11)

To a portion of the derivatized CPG support (9) with a total inosine loading of 0.31 mmol, was added DMAP (1.08 mmol), 9-fluorenylmethyl chloroformate (Fmoc-Cl, 18.58 mmol) and anhydrous pyridine (110 mL). The reaction mixture was stirred at room temperature for 2 hours. The resulting CPG was collected on a glass-fritted funnel, washed successively with pyridine, methanol (2×) and acetonitrile (3×). In order to cap non-converted hydroxyl groups, the reaction product was then reacted with a mixture of equal volumes of N-methylimidazole in acetic anhydride (10%, v/v) and anhydrous pyridine on the fritted funnel. The product, compound (11), was then washed successively with pyridine (2×) and acetonitrile (3×) and dried in vacuo.

The loading value of CPG preparation (11) was determined to be 56 μmol/g by cleaving off the Fmoc groups in a test sample (piperidine (20%, v/v) in DMF, 15 minutes at room temperature), which were then quantified photometrically at 301 nm.

Example 4

Preparation of the 2'/3'-Lev-protected Universal Solid Support (12)

A portion of the derivatized CPG support (9) with a total inosine loading of 5.5 mmol was suspended in a solution of DMAP (17.85 mmol) in dioxane (700 mL). Diisopropylcarbodiimide (526 mmol) and levulinic acid (420 mmol) were added and the reaction mixture was stirred at room temperature for 2 hours. The resulting CPG was collected on a glass-fritted funnel, washed successively with dioxane (3×), methanol (2×) and acetonitrile (3×). To cap non-converted hydroxyl groups, it was finally reacted with a mixture of equal volumes of N-methylimidazole in acetic anhydride (10%, v/v) and anhydrous pyridine on the fritted funnel. The product, compound (12) was washed successively with pyridine (2×) and acetonitrile (3×) and dried in vacuo. The loading value of compound 12 was determined to be 65 μmol/g by cleaving off the inosine moieties in a test sample (aq. LiOH (1 M), stirring for 10 minutes at room temperature), and subsequent photometrical quantification at 254 nm.

Example 5

General Procedure for the Tandem Synthesis of Oligonucleotides

The following example provides a general method for the tandem synthesis of oligonucleotides. For purposes of illustration this example describes the synthesis of two different oligonucleotides on a common solid support using the method of this invention, however, the method can be extended to the synthesis of an unlimited number of different oligonucleotides.

Prior to the automated oligonucleotide synthesis the solid support mixtures are prepared as follows:

1. Mixture of the DMT—or alternatively the methoxyethylidene-modified universal CPG (10) or (8) and the levulinyl-protected universal CPG (12): For the synthesis of a 1:1 mixture (mol/mol) of the two oligonucleotides, a 50:50 mixture of the two CPG types was used with regard to the respective loading values. The mixing of the component solid supports was conducted in a rotary evaporator flask on the evaporator with low speed at room temperature.

2. Mixture of the DMT—or alternatively the methoxyethylidene-modified universal CPG (10) or (8) and the Fmoc-protected universal CPG (11): For the synthesis of a 1:1 mixture (mol/mol) of the two oligonucleotides, a 60-70:40-30 mixture of the two CPG types was used with regard to the respective loading values. The mixing of the component solid supports was conducted in a rotary evaporator flask on the evaporator with low speed at room temperature. The excess of the component solid support (11) was applied to compensate for the partial loss of Fmoc-protection during the oligonucleotide synthesis. Thus, the optimal amount of (11) added depends on the size of the intended oligonucleotide to be synthesized first in the tandem oligonucleotide synthesis.

The solid support mixtures, prepared as described above, were packed into the reaction columns for an Applied Biosystems model 394 synthesizer. The synthesizer was used at 1 µmol scale. The synthesis protocol supplied by the instrument manufacturer was followed with the exception of the capping step after the synthesis of the first oligonucleotide and the subsequent removal of either the Fmoc- or levulinyl protective group, which were conducted as described below:

1. Synthesis of the first oligonucleotide in trityl-off mode;
2. Capping of the oligonucleotide with a mixture (1:1, v/v) of N-methylimidazole in acetic anhydride (10%, v/v) and anhydrous pyridine (600 µL) for 1 minute at room temperature;
3. Washing of the solid support with acetonitrile;
4. Removal of the Fmoc or levulinyl protective group on solid support:
Fmoc group: treatment with piperidine (20%, v/v) in DMF (300 µL) for 1 minute at room temperature
Levulinyl group: treatment with a 0.5 M solution of hydrazinium hydrate in a mixture (3:2, v/v) of pyridine and glacial acetic acid (300 µL) for 1 minute at room temperature;
5. Washing of the solid support with acetonitrile;
6. Synthesis of the second oligonucleotide in trityl-off mode;
7. Cleavage of the oligonucleotides off the solid support and deprotection by treatment with a mixture (1:1, v/v) of aq. MeNH$_2$ (40%, v/v) and aq. NaOAc (3 M) at 75° C. for 1 hour; and
8. Purification via ethanol precipitation according to standard procedures.

Example 6

Synthesis of Primer Pairs Consisting of 8mer to 15mer Oligodeoxynucleotides

The following primer pairs were synthesized according to the general procedure described in Example 5 using composite solid supports derived from the solid support components (8) and (12).

1. 10mer and 13mer primer pair of the sequences: d(GGGTGTTGTC)(SEQ ID NO:1) and d(GCTTACATTT-TAG)(SEQ ID NO:2);
2. 12mer and 15mer primer pair of the sequences: d(TCTT-TACACTTC)(SEQ ID NO:3) and d(TCTAACAGGGTGT-TG)(SEQ ID NO:4); and
3. 8mer and 12mer primer pair of the sequences: d(TAAAGGGA) and d(TTCTAGTTATCG)(SEQ ID NO:5).

All three pairs of oligonucleotides were characterized by gel electrophoresis (15% acrylamide, constant power of 250 Watt), as depicted in FIG. 5, and by RP-HPLC (VWR "Chromolith" column, TEAA (0.05 M)/acetonitrile gradient, detection at 260 nm).

Example 7

Synthesis of a 23mer and 25mer Oligodeoxynucleotide Sequencing Primer Pair

The following primer pair for sequencing was prepared according to the general procedure described in Example 5 using a composite solid support derived from the solid support components (8) and (12):

```
primer  d(CATCTGTAGTCTTTCACCTGTTT);    (SEQ ID NO: 6)
1:

primer  d(ACCTCACAAGATGTTCAAAAGCCAT).  (SEQ ID NO: 7)
2:
```

Both oligonucleotides were characterized by RP-HPLC and gel electrophoresis (both analytical methods were applied as described in Example 6), and AX-HPLC ("Mini-Q" column (Pharmacia), gradient: 20% to 60% solvent B in 30 minutes; solvent A: aqueous NaOH (10 mM) with acetonitrile (20%, v/v), solvent B: solvent A with NaCl (1 M); flow: 0.4 mL/min; detection at 260 nm).

Both primers 1 and 2 were identified on the above-mentioned RP-HPLC system. In addition, they were positively identified by comparing their electrophoretical mobility with those of the corresponding oligonucleotides, which were separately prepared according to standard protocols, as depicted in FIG. 6.

The identity of the target molecules was also confirmed by MALDI-TOF mass spectroscopy (matrix: 3-hydroxypicolinic acid in water/acetonitrile (1:1, v/v), using a Bruker "Biflex-III" mass spectrometer): m/z calculated for primer 1: 6946.57, found: 6947.4; m/z calculated for primer 2: 7603.05, found: 7605.

Example 8

PCR Assays Applying Tandemly Synthesized Primer Pairs

The following primer pairs were synthesized according to the general procedure described in Example 5 using composite solid supports derived from the solid support components (8) and (12):

```
primer pair #1:
d(TAATGTGTGTGCTTACATTTTAGGG)     (SEQ ID NO: 8)
and d(TTCATTGCTACTGGGGTGTTGTC);      (SEQ ID NO: 9)

primer pair #2:
d(GCTTTCATCAAGTTTATCCCAACC)      (SEQ ID NO: 10)
and d(CCCATCAATCTTTTTCTTTACACTTC).   (SEQ ID NO: 11)
```

The PCR experiments were performed in a MJ Research Engine Block thermalcycler. The PCR reactions were set up as follows: In a total volume of 25 μL each tube contained 1 unit of taq polymerase (Amplitaq Gold (Applied Biosystems)) in 'Gold buffer' (final concentrations: 15 mM Tris-HCl, 50 mM KCl, pH 8.0 (Applied Biosystems)) containing 200 μM each of dATP, dGTP, dCTP and dTTP.

The PCR experiments applying primer pair #1 as well as those applying primer pair #2 were carried out with female human genomic DNA as template and under the following three different sets of conditions:

C: 4 mM $MgCl_2$, primer concentration 0.1 μM, 10 ng template;

D: 4 mM $MgCl_2$, primer concentration 0.25 μM, 10 ng template; and

E: 6 mM $MgCl_2$, primer concentration 0.5 μM, 20 ng template

For reference purposes each of the experiments was duplicated employing primers that were individually synthesized with standard oligonucleotide synthesis protocols. The reactions were initiated at 95° C. for 7 minutes, followed by 30 cycles of denaturation at 94° C. for 0.5 minutes, annealing at 61° C. for 0.5 minutes and elongation at 72° C. for 0.5 minutes. The PCR products were analyzed via gel electrophoresis (3% agarose gel containing ethidium bromide) as depicted in FIG. 7. The presence of the expected PCR products of 182 bp for primer pair #1 and approximately 190-195 bp for the primer pair #2 is clearly visible (lanes no. 1-4). The PCR amplicon product bands are of similar strength and quality as the bands obtained with the primers that were individually synthesized by conventional means (lanes no. 5).

Example 9

Tandem Synthesis of Oligodeoxynucleotides Using a Composite Support

Prior to the automated oligonucleotide synthesis the solid support mixtures were prepared as follows:

Preparation of a ternary composite support comprising the methoxyethylidene-modified universal CPG (10), the Fmoc-protected universal CPG (11), and the levulinyl-protected universal CPG (12): In order to synthesize a 1:1:1 mixture (mol/mol/mol) of the three oligonucleotides, a 33:34:33 mixture of the three CPG types was used with regard to the respective loading values. The mixing of the component solid supports was conducted in a rotary evaporator flask on the evaporator with low speed at room temperature.

Tandem Synthesis of 3 Oligonucleotides on a Ternary Composite Support:

A solid support mixture, prepared as described above, was packed into the reaction column for an Applied Biosystems model 394 synthesizer. The synthesizer was used at a 1 μmol scale. The synthesis protocol supplied by the instrument manufacturer was followed with the exception of the capping steps after the synthesis of the first and second oligonucleotide and the subsequent steps to remove the Fmoc- and the levulinyl-protective groups, respectively, which were conducted as described below:

1. Synthesis of the first oligonucleotide: the 9mer d(TTTTTTTTT) in trityl-off mode;

2. Capping of this first oligonucleotide with a mixture (1:1, v/v) of N-methylimidazole in acetic anhydride (10%, v/v) and anhydrous pyridine anhydride acetic acid: N-methylimidazole (600 μL) for 1 minute at room temperature;

3. Washing of the solid support with acetonitrile;

4. Removal of the Fmoc group on solid support by a treatment with piperidine (20%, v/v) in DMF (300 μL) for 1 minute at room temperature;

5. Washing of the solid support with acetonitrile;

6. Synthesis of the second oligonucleotide: the 12mer d(TTTTTTTTTTTT)(SEQ ID NO:12) in trityl-off mode;

7. Capping of the oligonucleotide with a mixture (1:1, v/v) of N-methylimidazole in acetic anhydride (10%, v/v) and anhydrous pyridine anhydride acetic acid (600 μL) for 1 minute at room temperature;

8. Washing of the solid support with acetonitrile;

9. Removal of the levulinyl group on solid support by a treatment with a 0.5 M solution of hydrazinium hydrate in a mixture (3:2, v/v) of pyridine and glacial acetic acid (300 μL) for 1 minute at room temperature;

10. Washing of the solid support with acetonitrile;

11. Synthesis of the third oligonucleotide: the 15mer d(TTTTTTTTTTTTTTT) (SEQ ID NO:13) in trityl-off mode;

12. Cleavage of the oligonucleotides off the solid support and deprotection by treatment with a mixture (1:1, v/v) of aq. $MeNH_2$ (40%, v/v) and aq. NaOAc (3 M) at 75° C. for 1 hour; and 13. Purification via ethanol precipitation according to standard procedures.

The three oligonucleotides synthesized were characterized by gel electrophoresis and AX-HPLC. The latter was performed according to the method described in Example 7 and the corresponding chromatogram is depicted in FIG. 8.

Example 10

Tandem Synthesis on a Homogeneous Support Using a Universal CPG with Anchor Groups that are Partly Levulinyl Protected Preparation of the universal support with approximately 50% of the anchor groups protected by levulinyl groups: A portion of the derivatized CPG support (9) with a total inosine loading of 6.0 mmol was suspended in a solution of DMAP (0.15 mmol, 0.024 equivalents) in dioxane (700 mL). Diisopropylcarbodiimide (3.8 mmol, 0.63 eq.) and levulinic acid (3.0 mmol, 0.5 eq.) were added and the reaction mixture was stirred at room temperature for 2 hours. The resulting CPG was collected on a glass-fritted funnel, washed successively with dioxane (3×), methanol (2×) and acetonitrile (3×), and finally dried in vacuo.

The tandem synthesis of the two oligonucleotides:

```
d(CATCTGTAGTCTTTCACCTGTTT)     (SEQ ID NO: 6)
and d(ACCTCACAAGATGTTCAAAAGCCAT),  (SEQ ID NO: 7)
``` using the homogeneous support prepared as described above, was performed according to the general procedure described in Example 5. The synthesized oligonucleotides were characterized by gel electrophoresis and RP-HPLC.

Example 11

Purification by Gel Electrophoresis of Two Oligonucleotides Synthesized by the Tandem Method The following pair of primers was synthesized according to the general procedure described in Example 5 using a composite solid support derived from the solid support components (8) and (12):

```
                                             (SEQ ID NO: 14)
Primer 1:    d(ACGTTGGATGGTCTTCAGAGACATAGTTAAG)
and
                                             (SEQ ID NO: 15)
Primer 2:    d(ACGTTGGATGGTGGAGTAAGAGTAAATGTCC).
```

Figure 9:
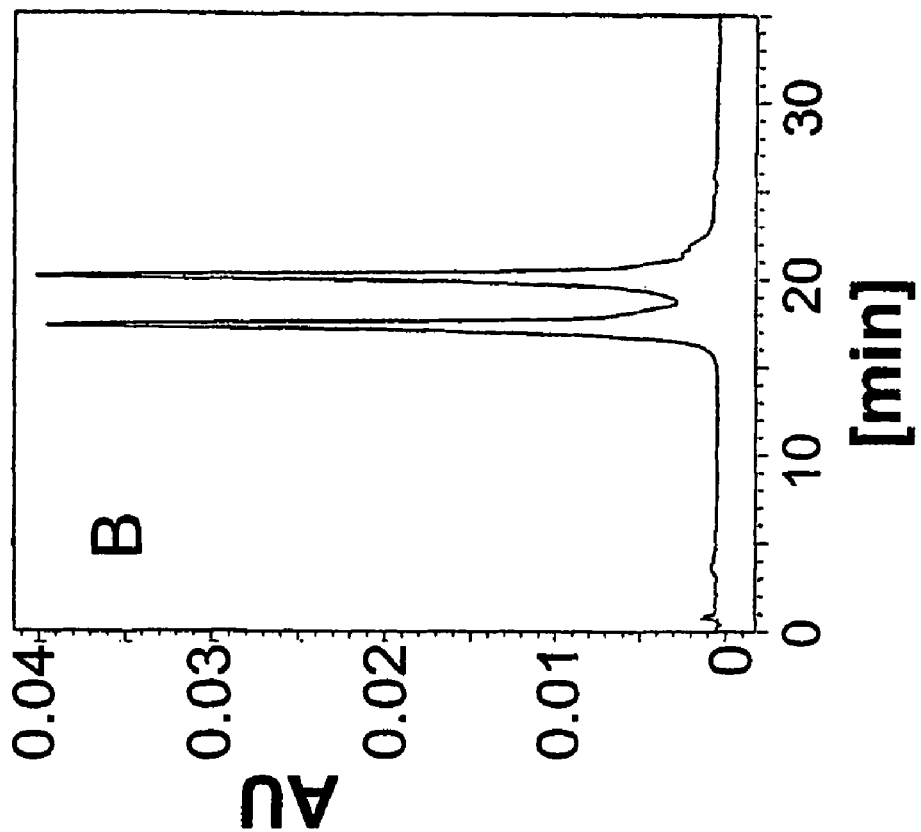
Figure 9:
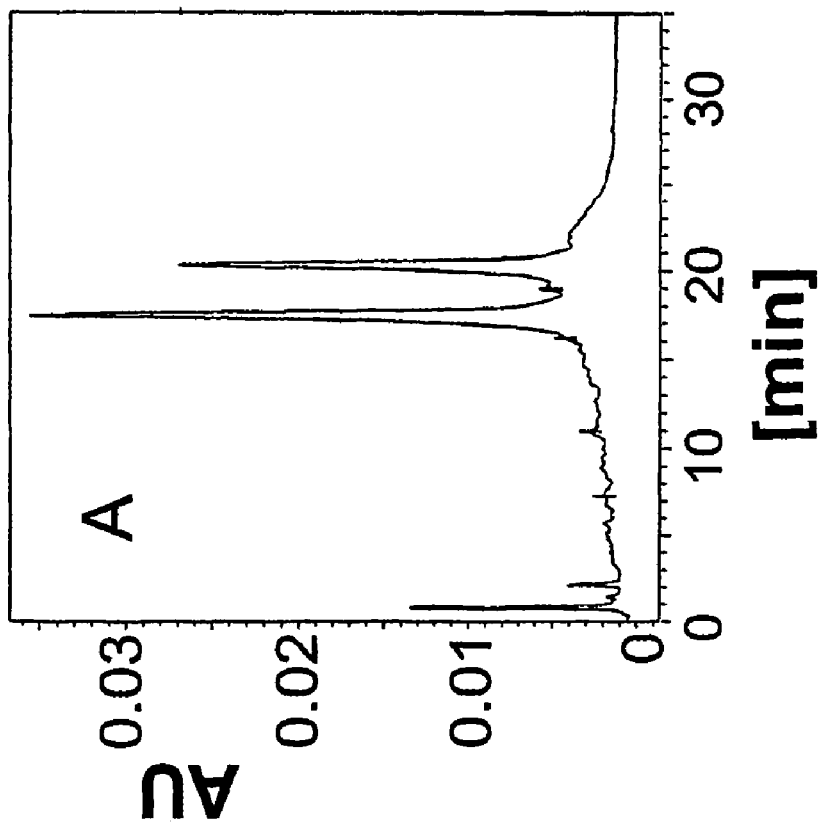

The pair of primers was purified by gel electrophoresis (15% acrylamide, constant power of <100 watts). The two oligonucleotides were characterized by RP-HPLC and successful purification was confirmed by comparing the chromatograms obtained before and after the gel electrophoresis, as depicted in FIG. 9.

Example 12

Preparation of Oligonucleotide Duplexes via Tandem Synthesizing Pairs of Complementary Oligonucleotides The following oligonucleotide pairs were synthesized according to the general procedure described in Example 5 using a composite solid support derived from the solid support components (8) and (12):

```
Pair #1
Oligonucleotide (A):

d(GCGACCGAGCCTGACCTCCAGTCCG)       (SEQ ID NO: 16)
and

Oligonucleotide (B):

d(CGGACTGGAGGTCAGGCTCGGTCGC).      (SEQ ID NO: 17)

Pair #2
Oligonucleotide (A):
d(ACGCTGCCAGTCACGGCGACCGCTC)       (SEQ ID NO: 18)

Oligonucleotide (B):
d(GAGCGGTCGCCGTGACTGGCAGCGT).      (SEQ ID NO: 19)
```

The duplexes formed by Pairs #1 and #2 were characterized by gel electrophoresis under non-denaturing conditions (without urea), as depicted in FIG. 10.

---

I claim:

1. A universal homogeneous solid support comprised of two or more independently selected universal linker subsets, each universal linker subset being independently covalently attached to a solid phase by a spacer moiety S, each universal linker subset comprising an anchor group, the anchor groups of two or more of the universal linker subsets being protected with protective groups selected from the group consisting of methoxyethylidene, dimethoxytrityl, levulinyl and 9-fluorenylmethoxycarbonyl that are orthogonal to each other, wherein the universal linkers are selected from the group of compounds having the following formula:

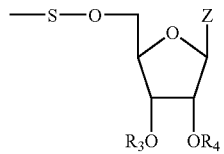

wherein
  S is selected from the group consisting of (a) —C(=O)—, (b) a diacyl moiety selected from the group consisting of oxalyl, malonyl, succinyl, and glutaryl, (c) a dialkyl moiety selected from methylidene, ethylidene and propylidene, (d) a alkylacyl moiety selected from —C(=O)—CH$_2$—, —CH$_2$—C(=O)—, —C(=O)—CH$_2$—CH$_2$— and —CH$_2$—CH$_2$—C(=O)—, —P(=O)(OH)— and (d) a protected phosphate moiety selected from compounds having the formula —P(=O)(OR$_6$)—, wherein R$_6$ is a phosphate protective group;
  Z is selected from the group consisting of a nucleobase, a hydrogen atom, and a methoxy group; and
  R$_3$ and R$_4$ are selected from the group consisting of a hydroxyl protective group, a hydrogen atom, and a capping group comprising an acetyl group, wherein a hydroxyl function at either the 2' or 3' position of the ring serves as the anchor group, and wherein the anchor group of only one universal linker subset optionally comprises a hydrogen atom.

2. The solid support of claim 1, wherein the phosphate protective group R$_6$ is 2-cyanoethyl.

3. The solid support of claim 1, wherein the orthogonal protective groups are dimethoxytrityl and 9-fluorenylmethoxycarbonyl.

4. The solid support of claim 1, wherein the orthogonal protective groups are methoxyethylidene and 9-fluorenylmethoxycarbonyl.

5. The solid support of claim 1, wherein the orthogonal protective groups are dimethoxytrityl and levulinyl.

6. The solid support of claim 1, wherein the orthogonal protective groups are methoxyethylidene and levulinyl.

7. The solid support of claim 1, wherein the nucleobase is selected from the group consisting of adenine, cytosine, guanine, thymine, and uracil.

8. The solid support of claim 7, wherein each nucleobase having an exocyclic amino group also comprises a protective group that protects the exocyclic amino group, the protective group selected from the group consisting of benzoyl, isobutyryl, and tert-butylphenoxyacetal.

9. The solid support of claim 1, wherein the 2' hydroxyl function serves as the anchor group, and R$_3$ and R$_4$ of each of the universal linker subsets are independently selected from the group consisting of (a) R$_3$ is the capping group and R$_4$ is one of the orthogonal protective groups; (b) R$_3$ is the capping group and R$_4$ is hydrogen; and (c) R$_3$ and R$_4$ together represent a methoxyethylidene moiety that bridges the oxygen atoms at the 2' and 3' positions, provided that only one (b) or only one (c) is present.

10. The solid support of claim 1, wherein the 3' hydroxyl function serves as the anchor group, and R$_3$ and R$_4$ of each of the universal linker subsets are independently selected from the group consisting of (a) R$_3$ is one of the orthogonal protective groups and R$_4$ is the capping group; (b) R$_3$ is hydrogen and R$_4$ is the capping group; and (c) R$_3$ and R$_4$ together represent a methoxyethylidene moiety that bridges the oxygen atoms at the 2' and 3' positions, provided that only one (b) or only one (c) is present.

* * * * *

UNITED STATES PATENT AND TRADEMARK OFFICE
CERTIFICATE OF CORRECTION

PATENT NO. : 7,615,629 B2 Page 1 of 1
APPLICATION NO. : 10/250492
DATED : November 10, 2009
INVENTOR(S) : Khalil Arar It is certified that error appears in the above-identified patent and that said Letters Patent is hereby corrected as shown below:

Claim 1, line 15 "and (d) a protected" should read -- and (e) a protected --

Signed and Sealed this

Sixteenth Day of March, 2010

David J. Kappos
*Director of the United States Patent and Trademark Office*

UNITED STATES PATENT AND TRADEMARK OFFICE
CERTIFICATE OF CORRECTION

PATENT NO. : 7,615,629 B2  Page 1 of 1
APPLICATION NO. : 10/250492
DATED : November 10, 2009
INVENTOR(S) : Khalil Arar It is certified that error appears in the above-identified patent and that said Letters Patent is hereby corrected as shown below:

Column 39, Claim 1, line 47 "and (d) a protected" should read -- and (e) a protected --

This certificate supersedes the Certificate of Correction issued March 16, 2010.

Signed and Sealed this

Sixth Day of April, 2010

David J. Kappos
*Director of the United States Patent and Trademark Office*